(12) United States Patent
Choi et al.

(10) Patent No.: US 11,382,868 B2
(45) Date of Patent: Jul. 12, 2022

(54) TRANSDERMAL UV-CURABLE HYDROGEL RESIN, HYDROGEL CURING THE SAME AND CATAPLASM CONTAINING THE SAME

(71) Applicant: ICURE PHARMACEUTICAL INC., Seoul (KR)

(72) Inventors: Young Kweon Choi, Seoul (KR); Yong Ho Oh, Seoul (KR); Seong Su Kim, Anseong-si (KR); Hwan Ki Ho, Pyeongtaek-si (KR); Song Mi Han, Seongnam-si (KR); Myung Jin Kim, Suwon-si (KR)

(73) Assignee: ICURE PHARMACEUTICAL INC., Seoul (KR)

( * ) Notice: Subject to any disclaimer, the term of this patent is extended or adjusted under 35 U.S.C. 154(b) by 333 days.

(21) Appl. No.: 16/077,355

(22) PCT Filed: Feb. 1, 2017

(86) PCT No.: PCT/KR2017/001051
§ 371 (c)(1),
(2) Date: Aug. 10, 2018

(87) PCT Pub. No.: WO2017/138710
PCT Pub. Date: Aug. 17, 2017

(65) Prior Publication Data
US 2019/0046463 A1    Feb. 14, 2019

(30) Foreign Application Priority Data
Feb. 11, 2016 (KR) .................. 10-2016-0015829

(51) Int. Cl.
| | |
|---|---|
| *A61K 9/70* | (2006.01) |
| *A61K 31/192* | (2006.01) |
| *C08L 101/00* | (2006.01) |
| *A61K 31/54* | (2006.01) |
| *A61K 31/167* | (2006.01) |
| *C08J 3/075* | (2006.01) |
| *A61K 45/06* | (2006.01) |
| *A61K 31/196* | (2006.01) |
| *A61K 47/10* | (2017.01) |
| *A61K 47/32* | (2006.01) |
| *A61K 47/38* | (2006.01) |

(52) U.S. Cl.
CPC .............. *A61K 9/703* (2013.01); *A61K 9/70* (2013.01); *A61K 31/167* (2013.01); *A61K 31/192* (2013.01); *A61K 31/196* (2013.01); *A61K 31/54* (2013.01); *A61K 45/06* (2013.01); *A61K 47/10* (2013.01); *A61K 47/32* (2013.01); *A61K 47/38* (2013.01); *C08J 3/075* (2013.01); *C08L 101/00* (2013.01)

(58) Field of Classification Search
CPC ........ A61K 9/703; A61K 31/54; C08L 101/00
See application file for complete search history.

(56) References Cited

U.S. PATENT DOCUMENTS

| | | | | |
|---|---|---|---|---|
| 2004/0242770 | A1* | 12/2004 | Feldstein | ............... A61L 15/60 |
| | | | | 525/54.3 |
| 2006/0198802 | A1* | 9/2006 | Ito | ........................... C08L 33/26 |
| | | | | 424/62 |
| 2014/0141056 | A1* | 5/2014 | Kubo | .................... A61K 9/7046 |
| | | | | 424/443 |

FOREIGN PATENT DOCUMENTS

| | | | | |
|---|---|---|---|---|
| JP | 2012062354 A | 3/2012 | | |
| JP | 2013525345 A | 6/2013 | | |
| JP | 2015059184 A | 3/2015 | | |
| KR | 10-2005-0078679 A | 8/2005 | | |
| KR | 10-2007-0011981 A | 1/2007 | | |
| KR | 10-2012-0096675 A | 8/2012 | | |
| KR | 20120096675 | * 8/2012 | ............... A61N 1/04 |
| KR | 10-2013-0124504 A | 11/2013 | | |
| KR | 10-2014-0006172 A | 1/2014 | | |
| WO | 2004093786 A2 | 11/2004 | | |
| WO | 2012142124 A2 | 10/2012 | | |

OTHER PUBLICATIONS

Lambers, Natural Skin Surface pH, Int. J. Cosmetic Sci. p. 359, Sep. 19 (Year: 2006).*
International Search Report for PCT/KR2017/001051, dated May 31, 2017.

* cited by examiner

*Primary Examiner* — Matthew P Coughlin
*Assistant Examiner* — Thurman Wheeler
(74) *Attorney, Agent, or Firm* — Sughrue Mion, PLLC

(57) ABSTRACT

The present invention relates to a UV-curable hydrogel resin for transdermal administration, a hydrogel prepared using the UV-curable hydrogel resin, and a cataplasm prepared using the UV-curable hydrogel resin. More particularly, the present invention relates to a hydrogel resin with an optimal composition and composition ratio which allows increase in a water content of a hydrogel applied as a drug layer of a cataplasm, skin irritation mitigation, and crosslinking degree adjustment for adhesion control and is capable of controlling drug releasing property and transdermal absorbability, a hydrogel prepared by UV-hardening the hydrogel resin, and a cataplasm including the hydrogel.

13 Claims, No Drawings

TRANSDERMAL UV-CURABLE HYDROGEL RESIN, HYDROGEL CURING THE SAME AND CATAPLASM CONTAINING THE SAME

CROSS REFERENCE TO RELATED APPLICATIONS

This application is a National Stage of International Application No. PCT/KR2017/001051, filed Feb. 1, 2017, claiming priority based on Korean Patent Application No. 10-2016-0015829, filed Feb. 11, 2016.

TECHNICAL FIELD

The present invention relates to a hydrogel resin for transdermal administration prepared using ultraviolet light (UV), a hydrogel prepared by curing the hydrogel resin using ultraviolet light, and a cataplasm including the hydrogel, and more particularly to a hydrogel containing a large amount of water to alleviate skin irritation, allowing easy crosslinking degree control thereof, having optimal drug releasing property and transdermal absorbability to exhibit an effect equivalent to that of oral administration, being capable of maintaining superior adhesion and elasticity, being capable of being easily prepared, and being capable of being shipped after cutting and packing, without a separate cutting or cooling process, immediately after crosslinking to allow easy production, and a cataplasm including the hydrogel.

BACKGROUND ART

Polyacrylic acid, which is prepared by metal complex ionic bonding, has biocompatibility and excellent adhesion to the human body. U.S. Pat. No. 4,320,040 (1982) discloses a method of preparing a hydrogel using acrylic acid or methacrylic acid along with polyvinyl alcohol. U.S. Pat. No. 5,223,569 (1993) also reports a hydrogel prepared with acrylic acid and starch. In particular, U.S. Pat. No. 4,200,561 (1980) proposes a method of preparing a hydrogel by crosslinking polyacrylic acid so as to increase water resistance against perspiration and the like generated from the human body, particularly a method of preparing a hydrogel using a gelling agent and a copolymer mixture including acrylic acid, ethacrylic acid, esterified acrylic acid, vinyl acetate, vinyl formate, and vinyl propionate. In addition, U.S. Pat. No. 3,937,680 (1976) proposes a method of using ethylene glycol dimethacrylate, methacrylic acid, and 2-hydroxyethyl methacrylate as crosslinking agents to highly maintain a water content.

Since a polyacrylic acid cataplasm crosslinked by metal complex ionic bonding has very long crosslinking time for metal complex ionic bonding, it cannot be rapidly released as a product. In addition, an aqueous polyvinyl alcohol solution, which is a synthetic polymer, can be crosslinked by formaldehyde, glutaraldehyde, etc. and can be gelled through repeated freezing and thawing. However, crosslinking by an aldehyde has problems that remaining aldehyde, which has not been completely eliminated, is toxic, the strength of a gel formed through repeated freezing and thawing is not high, and a long process time due to the repeated freezing and thawing causes product price rise.

To prepare a hydrogel using polyvinyl pyrrolidone by a chemical crosslinking method, polyvinyl pyrrolidone is dissolved in distilled water, and then a multifunctional monomer, such as ethylene glycol dimethacrylate, propylene glycol dimethacrylate, tetraethylene glycol dimethacrylate, or trimethylolpropane triacrylate, and a chemical initiator are added thereto, followed by heating. However, in the case of a chemical/thermal crosslinking method, there is a problem that unreacted initiator or crosslinking agent remains when reaction is terminated.

Therefore, there is a need for a manufacturing technology capable of shortening crosslinking time due to a crosslinking agent, not using a toxic solvent, and not containing unreacted initiator residue and crosslinking agent residue.

In the case of commercially available general hydrogels, metal complex ion crosslinking is mainly used. However, in this case, it takes a long period of about 1 to 3 weeks for complete crosslinking, and there is a lot of difficulty in adjusting adhesion and the strength of a gel. In addition, crosslinking is not achieved as desired under a condition of pH 7 or more. Due to these various problems, there is a lot of difficulty in adding various drugs to a hydrogel.

DISCLOSURE

Technical Problem

Therefore, the present invention has been made in view of the above problems, and it is one object of the present invention to shorten a long preparation time of a hydrogel used in a patch. To accomplish this, a hydrogel is cured using ultraviolet light, and thus, the curing time of hydrogel is greatly shortened, whereby productivity greatly increases. It is another object of the present invention to provide a hydrogel with an optimal composition and composition ratio allowing excellent skin absorption and transmission of drugs contained therein and having high adhesion to the skin, and a cataplasm including the hydrogel.

Technical Solution

In accordance with an aspect of the present invention, the above and other objects can be accomplished by the provision of a UV-curable hydrogel resin for transdermal administration. More particularly, the UV-curable hydrogel resin includes a hydrophilic polymer, an active ingredient, a wetting agent, solvent, a transdermal penetration facilitator, a UV initiator, and a UV crosslinking agent.

As a preferred embodiment of the present invention, the hydrogel resin of the present invention may include 5 to 60% by weight of a hydrophilic polymer, 0.1 to 15% by weight of an active ingredient, 0.6 to 80% by weight of a wetting agent, 13.5 to 90% by weight of a solvent, 0.5 to 25% by weight of a transdermal penetration facilitator, 0.01 to 2.0% by weight of a UV initiator, and 0.01 to 2.0% by weight of a UV crosslinking agent.

As a preferred embodiment of the present invention, the hydrogel resin of the present invention may further include a pH regulator.

As a preferred embodiment of the present invention, the hydrophilic polymer in the hydrogel resin of the present invention may include one or more selected from polyvinyl alcohol, polyvinyl pyrrolidone, a polyvinyl pyrrolidone/vinyl acetate copolymer, a vinyl ether/anhydric maleic acid copolymer, an isobutylene/anhydric maleic acid copolymer, a methoxyethylene/anhydric maleic acid copolymer, a methacrylic acid/butyl acrylate copolymer, alginate, hydroxyethyl methacrylate, hydroxyethyl cellulose, hydroxypropyl cellulose, hydroxypropyl methylcellulose, ethyl cellulose, methyl cellulose, sodium carboxymethyl cellulose, a carboxyvinyl copolymer, polyethylene oxide, polyethylene glycol, polyacrylamide, polyhydroxyethyl methacrylate, polydioxolane, polyacrylic acid, sodium polyacrylate, polyvinyl acrylate, polyacryl acetate, and polyvinyl chloride.

As a preferred embodiment of the present invention, the active ingredient in the hydrogel resin of the present invention may include one or more selected from lidocaine, lidocaine hydrochloride, loxoprofen, loxoprofenate, ketoprofen, flurbiprofen, diclofenac, diclofenac salt, indomethacin, piroxicam, meloxicam, naproxen, ibuprofen, felbinac, menthol, glycol salicylate, methyl salicylate, pepper extracts, vanillyl nonylamide, butyl vinyl ether, centella asiatica, fusidic acid, fusidate, acrinol, Pueraria mirifica, heparin, heparinate, and allantoin.

As a preferred embodiment of the present invention, the wetting agent in the hydrogel resin of the present invention may include one or more selected from glycerin, 1,3-butylene glycol, propylene glycol, polypropylene glycol, sorbitol, mannitol, ethylene glycol, diethylene glycol, polyethylene glycol, and hyarulonic acid.

As a preferred embodiment of the present invention, the transdermal penetration facilitator in the hydrogel resin of the present invention may include one or more selected from propylene glycol, dipropylene glycol, polyethylene glycol, polyoxyethylene monooleate, polyglyceryl diisostearate, glycerin monooleate, polyoxyethylene sorbitan, N-methyl-2-pyrrolidone, N-carprylyl-2-pyrrolidone, N-dodecyl-2-pyrrolidone, lauryl pyrrolidone, lauryl alcohol, glycerol lauryl alcohol, oleyl alcohol, isopropyl myristrate, sorbitan monooleate, propylene monolaurate, propylene mono-oleate, oleoyl macrogolglyceride, oleic acid, lauroyl macrogol glyceride, linoleoyl macrogol glyceride, propylene glycol caprylate, propylene glycol caprate, sorbitan monostearate monooleate, glycerol monolaurate, glycerol monooleate, propylene glycol monolaurate, propylene glycol monocaprylate, sorbitan monolaurate, lauryl lactate, caprylic triglyceride, capric triglyceride, corn oil PEG-8 ester, corn oil PEG-6 ester, and triacetin.

As a preferred embodiment of the present invention, the UV initiator in the hydrogel resin of the present invention may include one or more selected from a ketone-based UV initiator, a thioxantone-based UV initiator, a benzophenone-based UV initiator, a coumarin-based UV initiator, a thiazoline-based UV initiator, a rhodanine-based UV initiator, and other UV initiators.

As a preferred embodiment of the present invention, the ketone-based UV initiator may include one or more of 1-hydroxy-cyclohexyl-phenyl-ketone, 2-hydroxy-2-methyl-1-phenyl-1-propanone, 2-hydroxy-1-[4-(2-hydroxyethoxy)phenyl]-2-methyl-1-propanone, 2-benzyl-2-(dimethylamino)-1-[4-(4-morpholinyl)phenyl]-1-butanone, and 2-methyl-1-[4-(methylthio)phenyl]-2-(4-morpholinyl)-1-propanone.

As a preferred embodiment of the present invention, the thioxantone-based UV initiator may include one or more of thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxy-carbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]-thioxanthone, 1,3-dimethyl-3-hydroxy-9H-thioxanthone-9-one 2-ehylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboxamide, 1-phenoxythioxanthone, 6-ethoxycarbonyl-2-methoxythioxanthone, 6-ethoxycarbonyl-2-methylthioxanthone, thioxanthone-2-carboxylic acid polyethylene glycol ether, and 2-hydroxy-3-(3,4-dimethyl-9-oxo-9H-thioxanthone-2-2-yloxy)-N,N,N-trimethyl-1-propanaminiumchloride.

As a preferred embodiment of the present invention, the benzophenone-based UV initiator may include one or more of benzophenone, 4-phenyl benzophenone, 4-methoxy benzophenone, 4,4'-dimethyl benzophenone, 4,4'-dichlorobenzophenone, 4,4'-bis(dimethylamino)-benzophenone, 4,4'-bis(diethylamino)benzophenone, 4,4'-bis(methylethylamino)benzophenone, 4,4'-bis(p-isopropylphenoxy)benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoyl-phenylsulfanyl)-phenyl]-2-methyl-2(toluene-4-sulfonyl)-propane-1-one, 4-benzoyl-N,N,N-trimethylbenzenemethanaminium chloride, 2-hydroxy-3-(4-benzoyl-phenoxy)-N,N,N-trimethyl-1-propaneaminium chloride monohydrate, 4-(13-acryloyl-1,4,7,10,13-pentaoxatridecyl)-benzophenone, and 4-benzoyl-N,N-dimethyl-N-[2-(1-oxo-2-prophenyl)oxy]ethyl-benzenemethanaminium chloride.

As a preferred embodiment of the present invention, the coumarin-based UV initiator may include one or more of coumarin 1, coumarin 2, coumarin 6, coumarin 7, coumarin 30, coumarin 102, coumarin 106, coumarin 138, coumarin 152, coumarin 153, coumarin 307, coumarin 314, coumarin 314T, coumarin 334, coumarin 337, coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, and 7-diethylamino-3-phenylcoumarin.

As a preferred embodiment of the present invention, the thiazoline-based UV initiator may include one or more of 3-(aroylmethylene)-thiazolines such as 3-methyl-2-benzoylmethylene-β-naphthothiazoline, 3-methyl-2-benzoylmethylene-benzothiazoline, and 3-ethyl-2-propionylmethylene-β-naphtholthiazoline.

As a preferred embodiment of the present invention, the rhodanine-based UV initiator may include one or more of 4-dimethylaminobenzalrhodanine, 4-diethylaminobenzalrhodanine, and 3-ethyl-5-(3-octyl-2-benzothiazolinylidene)-rhodanine.

As a preferred embodiment of the present invention, the other UV initiators may include one or more selected from phenylacetophenone, hydroxy dimethyl acetophenone, 4,4'-bis(dimethylamino)benzyl, methylbenzoylformate, diphenyl (2,4,6-trimethylbenzoyl)-phosphine oxide, phenyl bis(2, 4,6-trimethyl benzoyl), oxy-phenyl-acetic acid-2-[2-oxo-2-phenyl-acetoxy-ethoxy]-ethyl ester, oxy-phenyl-acetic acid-2-[2-hydroxy-ethoxy]-ethyl ester, 4-cyclopentadiene-1-yl) bis[2,6-difluoro-3-(1-H-pyrrole-1-yl)phenyl] titanium, 2-acetylnaphthalene, 2-naphthalaldehyde, iodonium salt, dicylic acid derivatives, 9.10-anthraquinone, anthracene, pyrene, aminopyrene, perylene, phenanthrene, phenanthrenequinone, 9-fluorenone, dibenzosuberone, curcumin, xanthone, thiomichler's ketone, 2,5-bis(4-diethylaminobenzyl-lidene)cyclopentanone, 2-(4-dimethylamino-benzyllidene))-indan-1-one, α-(4-dimethylaminobenzyllidene))ketone such as 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)-phthalimide, phenothiazine, methylphenothiazine, N-phenylglycine, amines such as triethanolamine and N-methyldiethanolamine, ethyl-p-dimethylaminobenzoate, 2-(dimethylamino)ethylbenzoate, 2-ethylhexyl-p-dimethylaminobenzoate, octyl-para-N, N-dimethylaminobenzoate, N-(2-hydroxyethyl)-N-methyl-para-toluidine, butoxyethyl 4-dimethylaminobenzoate, 4-dimethyl aminoacetophenone, triethanolamine, methyl di ethanol amine, dimethylaminoethanol, 2-(dimethylamino) ethyl benzoate, poly(propylene glycol)-4-(dimethylamino) benzoate, and michler's ketone.

As a preferred embodiment of the present invention, the UV crosslinking agent in the hydrogel resin of the present invention may include one or more selected from benzyl methacrylate, lauryl methacrylate, isodecyl methacrylate, phenoxy methacrylate, 2-hydroxyethyl methacrylate, tetrahydro furfuryl methacrylate, cetyl(C16) methacrylate, stearyl methacrylate, methoxyPEG500 methacrylate, methoxyPEG600 methacrylate, methoxyPEG1000 methacrylate, 1,6-hexandiol dimethacrylate, butadiene dimethacrylate, neopentylglycol dimethacrylate, ethyleneglycoldimethacrylate, diethyleneglycol dimethacrylate, triethyleneglycol dimethacrylate, tetraethyleneglycol dimethacrylate, bisphenol A(EO)4 dimethacrylate, bisphenol A(EO)3 dimethacrylate, bisphenol A(EO)10 dimethacrylate, bisphenol A(EO)30 dimethacrylate, 1,3-butyleneglycol dimethacrylate, polyethylene glycol 400 dimethacrylate, polyethylene glycol 200 dimethacrylate, PPG1000(EO)15 dimethacrylate, PPG1000(EO)3 dimethacrylate, trimethylolpropane trimethacrylate, benzyl acrylate, lauryl acrylate, isodecyl acrylate, phenol(EO) acrylate, phenol(EO)2 acrylate, phenol(EO)4 acrylate, phenol(EO)6 acrylate, tetrahydro furfuryl acrylate, nonyl phenol(EO)4 acrylate, nonyl phenol(EO)8 acrylate, nonyl phenol(EO)2 acrylate, ethoxyethoxy ethyl acrylate, stearyl acrylate, 1,6-hexandiol diacrylate, 1,6-hexandiol(EO) diacrylate, butanediol diacrylate, hydroxy pivalic acid neopentyl glycol diacrylate, tripropylene glycol diacrylate, dipropylene glycol diacrylate, bisphenol A(EO)4 diacrylate, bisphenol A(EO)3 diacrylate, tricyclodecane dimethanol diacrylate, tetraethylene glycol diacrylate, polyethylene glycol 400 diacrylate, polyethylene glycol 200 diacrylate, polyethylene glycol 300 diacrylate, polyethylene glycol 600 diacrylate, polypropylene glycol 400 diacrylate, polypropylene glycol 750 diacrylate, bisphenol A(EO)10 diacrylate, bisphenol A(EO)30 diacrylate, tris (2-hydroxy ethyl)isocyanurate diacrylate, trimethylolpropane triacrylate, trimethylolpropane(EO)3 triacrylate, trimethylolpropane(EO)6 triacrylate, trimethylolpropane (EO)9 triacrylate, trimethylolpropane(EO)15 triacrylate, glycerin propoxylated triacrylate, pentaerythritol triacrylate, trimethylolpropane(PO)3 triacrylate, tris(2-hydroxy ethyl) isocyanurate triacrylate, pentaerythritol n-EO tetraacrylate, pentaerythritol tetraacrylate, dipentaerythritol pentaacrylate, dipentaerythritol hexaacrylate, caprolactone acrylate, O-phenylphenol EO acrylate, and methylene bisacrylamide.

As a preferred embodiment of the present invention, the pH regulator in the hydrogel resin of the present invention may include one or more selected from citric acid, acetic acid, malic acid, succinic acid, tartaric acid, lactic acid, triethanolamine, diisopropanolamine, and diethanolamine.

As a preferred embodiment of the present invention, the hydrogel resin of the present invention may have a pH of 3 to 9.

It is another objective of the present invention to provide a cured product by produced by UV-hardening the hydrogel resin, i.e., a hydrogel.

As a preferred embodiment of the present invention, the hydrogel of the present invention may exhibit an adhesion of 50 gf to 120 gf under a peel strength test.

It is another objective of the present invention to provide a cataplasm that includes a drug layer including the aforementioned various UV-curable hydrogel types; and a drug support layer.

As a preferred embodiment of the present invention, the drug support layer in the cataplasm of the present invention may include one or more selected from a polyurethane film, a porous film, a perforated film, a fabric, a nonwoven fabric, and a foam.

As a preferred embodiment of the present invention, the drug layer may have an average thickness of 20 μm to 2,000 μm, and the drug support layer may have an average thickness of 7 μm to 500 μm.

As a preferred embodiment of the present invention, the cataplasm of the present invention may further include a peel layer. Here, the peel layer, the drug layer, and the drug support layer may be sequentially stacked.

As a preferred embodiment of the present invention, the peel layer may include a polymer film coated with a silicone resin or a fluorine resin. Here, the polymer film may include one or more polymer compounds selected from polyester; polyvinyl chloride; polyvinylidenechloride; polyethyl eneterephthalate; and copolymers thereof.

As a preferred embodiment of the present invention, the peel layer may have an average thickness of 15 μm to 500 μm.

As a preferred embodiment of the present invention, the cataplasm of the present invention may be used for anti-inflammation and analgesic effects.

It is yet another objective of the present invention to provide a method of preparing a cataplasm, the method including a first step of preparing a hydrogel resin; a second step of coating the hydrogel resin on a peel film; a third step of stacking a support on the coated hydrogel resin; and a fourth step of irradiating the support with UV of 2,000 to 8,000 mW/cm$^2$ for 3 minutes to 10 minutes to harden the hydrogel resin.

Advantageous Effects

A UV-curable hydrogel for transdermal administration of the present invention is prepared using a non-toxic solvent and is capable of containing a large amount of water, thereby alleviating skin irritation. In addition, since a crosslinking degree of the UV-curable hydrogel can be easily adjusted, it is easy to control adhesion and elasticity thereof. In addition, drug releasing property and transdermal absorbability can be controlled through adjustment of a crosslinking degree of the hydrogel, and a cataplasm having superior skin permeation rate and skin permeation speed can be provided. In addition, a cataplasm can be easily produced using the hydrogel of the present invention. The cataplasm prepared using the hydrogel of the present invention can be stored for a long time, compared to a cataplasm based on a hydrogel formed by metal complex ionic bonding, whereby it is easy to secure stability thereof. Further, since the cataplasm can be shipped after cutting and packing, without a separate cutting or cooling process, immediately after crosslinking of the hydrogel, it is possible to provide a cataplasm having superior economic efficiency and marketability.

BEST MODE

Hereinafter, the present invention is described in more detail.

A method of preparing a cataplasm of the present invention includes a first step of preparing a hydrogel resin; a second step of coating the hydrogel resin on a peel film; a third step of stacking a support on the coated hydrogel resin; and a first step of irradiating the support with UV to harden the hydrogel resin.

In the first step, the hydrogel resin may be prepared by stirring and crosslinking a mixture of a hydrophilic polymer, an active ingredient, a wetting agent, a solvent, a transdermal penetration facilitator, a UV initiator, and a UV crosslinking agent at room temperature (15° C. to 35° C.) at 150 to 1650 rpm for 5 to 12 hours such that the compositions are sufficiently dissolved in a solvent.

The hydrophilic polymer of the hydrogel resin ingredients used in the first step serves to impart viscoelasticity to the hydrogel and maintain water content. The hydrophilic polymer may be included in an amount of 5 to 60% by weight, preferably 5 to 40% by weight, more preferably 8 to 35% by weight, based on a total weight of the hydrogel resin. Here, when the content of the hydrophilic polymer is less than 5% by weight, a water content and viscoelasticity of the hydrogel might not be maintained. On the other hand, when the content of the hydrophilic polymer is greater than 60% by weight, viscosity may too highly increase, which hinders the coating of the second step. In addition, crosslinking property may be greatly decreased.

In addition, as the hydrophilic polymer, one or more selected from polyvinyl alcohol, polyvinyl pyrrolidone, a polyvinyl pyrrolidone/vinyl acetate copolymer, a vinyl ether/anhydric maleic acid copolymer, an isobutylene/anhydric maleic acid copolymer, a methoxyethylene/anhydric maleic acid copolymer, a methacrylic acid/butyl acrylate copolymer, alginate, hydroxyethyl methacrylate, hydroxyethyl cellulose, hydroxypropyl cellulose, hydroxypropyl methylcellulose, ethyl cellulose, methyl cellulose, sodium carboxymethyl cellulose, a carboxyvinyl copolymer, polyethylene oxide, polyethylene glycol, polyacrylamide, polyhydroxyethyl methacrylate, polydioxolane, polyacrylic acid, sodium polyacrylate, polyvinyl acrylate, polyacryl acetate, polyvinyl chloride and polyacrylamide may be used. Preferably, one or more selected from polyvinyl pyrrolidone, a polyvinyl pyrrolidone/vinyl acetate copolymer, hydroxypropyl cellulose, hydroxypropyl methylcellulose, hydroxyethyl methacrylate, sodium polyacrylate, polyacrylic acid, sodium carboxymethyl cellulose, and polyacrylamide may be used. More preferably, the hydrophilic polymer may be prepared by mixing 5 to 100 parts by weight, preferably 10 to 50 parts by weight, of one or more selected from hydroxypropyl cellulose, sodium polyacrylate, polyacrylic acid, sodium carboxymethyl cellulose, and polyacrylamide with 100 parts by weight of polyvinylidone. As a particular example, a mixture of the hydrophilic polyvinyl pyrrolidone and sodium polyacrylate, a mixture of polyvinyl pyrrolidone and polyacrylic acid, a mixture of polyvinyl pyrrolidone and polyacrylamide, a mixture of polyvinyl pyrrolidone and polyvinyl alcohol, a mixture of polyvinyl pyrrolidone and sodium carboxymethyl cellulose, a mixture of polyvinyl pyrrolidone and hydroxyethyl cellulose, a mixture of polyvinyl pyrrolidone and hydroxypropyl cellulose, or a mixture of polyvinyl pyrrolidone and hydroxyethyl methacrylate may be used.

In addition, the hydrophilic polymer may be a polymer treated with a publicly known crosslinking agent or polymer.

As the active ingredient of the hydrogel resin ingredients used in the first step, an active ingredient, which has been used in the art, may be determined according to use of the hydrogel. Preferably, as the active ingredient, one or a mixture of two or more selected from lidocaine, lidocaine hydrochloride, loxoprofen, loxoprofenate, ketoprofen, flurbiprofen, diclofenac, diclofenac salt, indomethacin, piroxicam, meloxicam, naproxen, ibuprofen, felbinac, menthol, glycol salicylate, methyl salicylate, pepper extracts, vanillyl nonylamide, butyl vinyl ether, centella asiatica, fusidic acid, fusidate, acrinol, Pueraria mirifica, heparin, heparinate, and allantoin may be used. As a particular example, one or a mixture of two or more of lidocaine, lidocaine hydrochloride, loxoprofen, loxoprofenate, and the like having anti-inflammation and analgesic effects may be used.

In addition, the active ingredient may be included in an amount of 0.1 to 15% by weight, preferably 1 to 10% by weight with respect to a total weight of the hydrogel resin. When the content of the active ingredient is less than 0.1% by weight, effect due to addition of the active ingredient might not be exhibited due to too small amount thereof. On the other hand, when the content of the active ingredient is greater than 15% by weight, the excessive active ingredient hinders crosslinking, which may cause problems in preparing the hydrogel.

The wetting agent of the hydrogel resin ingredients used in the first step serves to maintain a wet state of a hydrogel, alleviate skin irritation, maintain constant cooling ability, and improve hydration of water. As the wetting agent, an agent generally used in the art may be used. Preferably, the wetting agent may include one or more selected from glycerin, 1,3-butylene glycol, propylene glycol, polypropylene glycol, sorbitol, mannitol, ethylene glycol, diethylene glycol, polyethylene glycol, and hyarulonic acid. More preferably, a mixture of glycerin and sorbitol mixed in a weight ratio of 1:0.2 to 0.5 may be used.

In addition, the wetting agent may be included in an amount of 0.6 to 80% by weight, preferably 5 to 50% by weight, more preferably 12 to 40% by weight based on a total weight of the hydrogel resin. When the content of wetting agent is less than 0.6% by weight, a sufficient wet state of the hydrogel might not be maintained. On the other hand, when the content of wetting agent is greater than 80% by weight, the hydrogel might not be hardened.

The solvent of the hydrogel resin ingredients used in the first step may be purified water, distilled water, or the like. The content of the solvent may be 13.5 to 90% by weight, preferably 18 to 70% by weight, more preferably 30 to 60% by weight, based on a total weight of the hydrogel resin.

The transdermal penetration facilitator of the hydrogel resin ingredients used in the first step serves to promote transdermal absorption of the active ingredient and sustain efficacy thereof. The transdermal penetration facilitator may be included in an amount of 0.5 to 25% by weight, preferably 0.5 to 23% by weight, more preferably 1 to 20% by weight, based on a total weight of the hydrogel resin. When the content of the transdermal penetration facilitator is less than 0.5% by weight, transdermal absorption of the active ingredient in the hydrogel may be greatly decreased. On the other hand, when the content of the transdermal penetration facilitator is greater than 25% by weight, adhesion of the hydrogel may be decreased.

As the transdermal penetration facilitator, only one or a mixture of two or more selected from propylene glycol, dipropylene glycol, polyethylene glycol, polyoxyethylene monooleate, polyglyceryl diisostearate, glycerin monooleate, polyoxyethylene sorbitan, N-methyl-2-pyrrolidone, N-carprylyl-2-pyrrolidone, N-dodecyl-2-pyrrolidone, lauryl pyrrolidone, lauryl alcohol, glycerol lauryl alcohol, oleyl alcohol, isopropyl myristrate, sorbitan mono-oleate, propylene monolaurate, propylene mono-oleate, oleoyl macrogolglyceride, oleic acid, lauroyl macrogol glyceride, linoleoyl macrogol glyceride, propylene glycol caprylate, propylene glycol caprate, sorbitan monostearate mono-oleate, glycerol monolaurate, glycerol monooleate, propylene glycol monolaurate, propylene glycol monocaprylate, sorbitan monolaurate, lauryl lactate, caprylic triglyceride, capric triglyceride, corn oil PEG-8 ester, corn oil PEG-6 ester, and triacetin may be used. Preferably, only one or a mixture of two or more selected from propylene glycol, dipropylene glycol, glycerin monooleate, polyoxyethylene sorbitan, N-methyl-2-pyrrolidone, sorbitan mono-oleate, isopropylmyristate, polyoxyethylene monooleate, glycerolmonooleate, propyleneglycolmonolaurate and polyglyceryl diisostearate may be used. More preferably, a mixture of propylene glycol and one selected from sorbitan monooleate, isopropylmyristate, polyoxyethylene monooleate, glycerolmonooleate, propyleneglycolmonolaurate, and polyglyceryl diisostearate mixed in a weight ratio of 1:0.03 to 0.5 may be used. In addition, more preferably, when the active ingredient is loxoprofen sodium and a salt thereof, a mixture of three or more selected from propylene glycol, glycerinmonooleate, glycerin monooleate, polyoxyethylene sorbitan, N-methyl-2-pyrrolidone, and laurylpyrrolidone may be used.

The UV initiator of the hydrogel resin ingredients used in the first step serves to initiate crosslinking reaction, causing hydrogel formation. As the UV initiator, only one or a mixture of two or more selected from a ketone-based UV initiator, a thioxantone-based UV initiator, a benzophenone-based UV initiator, a coumarin-based UV initiator, a thiazoline-based UV initiator, a rhodanine-based UV initiator, and other UV initiators may be used. In addition, the content of the UV initiator may be 0.01 to 2.0% by weight, preferably 0.025 to 1.5% by weight, more preferably 0.1 to 1.0% by weight, based on a total weight of the hydrogel resin. When the content of the UV initiator is less than 0.01% by weight, hardening time due to UV irradiation may be too long, whereby marketability may be decreased. In addition, a hardened hydrogel may exhibit poor viscoelasticity. On the other hand, the content of the UV initiator is greater than 2% by weight, a hardening speed may be too fast, whereby it may be difficult to control a hardening speed and adhesion may be decreased.

Examples of a UV initiator available in the present invention are particularly described as follows.

As the ketone-based UV initiator, only one or a mixture of two or more selected from α-hydroxy ketones, such as 1-hydroxy-cyclohexyl-phenyl-ketone, 2-hydroxy-2-methyl-1-phenyl-1-propanone, and 2-hydroxy-1-[4-(2-hydroxyethoxy)phenyl]-2-methyl-1-propanone and α-amino ketones, such as 2-benzyl-2-(dimethylamino)-1-[4-(4-morpholinyl)phenyl]-1-butanone and 2-methyl-1-[4-(methylthio)phenyl]-2-(4-morpholinyl)-1-propanone may be used.

As the thioxantone-based UV initiator, only one or a mixture of two or more selected from thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxycarbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]-thioxanthone, 1,3-dimethyl-3-hydroxy-9H-thioxanthone-9-one 2-ehylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboxamide, 1-phenoxythioxanthone, 6-ethoxycarbonyl-2-methoxythioxanthone, 6-ethoxycarbonyl-2-methylthioxanthone, thioxanthone-2-carboxylic acid polyethylene glycol ether, and 2-hydroxy-3-(3,4-dimethyl-9-oxo-9H-thioxanthone-2-2-yloxy)-N,N,N-trimethyl-1-propanaminiumchloride may be used.

As the benzophenone-based UV initiator, only one or a mixture of two or more selected from benzophenone, 4-phenyl benzophenone, 4-methoxy benzophenone, 4,4'-dimethyl benzophenone, 4,4'-dichlorobenzophenone, 4,4'-bis(dimethylamino)-benzophenone, 4,4'-bis(diethylamino)benzophenone, 4,4'-bis(methylethylamino)benzophenone, 4,4'-bis(p-isopropylphenoxy)benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-(4-benzoyl-phenylsulfanyl)-phenyl]-2-methyl-2(toluene-4-sulfonyl)-propane-1-one, 4-benzoyl-N,N,N-trimethylbenzenemethanaminium chloride, 2-hydroxy-3-(4-benzoyl-phenoxy)-N,N,N-trimethyl-1-propaneaminium chloride monohydrate, 4-(13-acryloyl-1,4,7,10,13-pentaoxatridecyl)-benzophenone, and 4-benzoyl-N,N-dimethyl-N-[2-(1-oxo-2-prophenyl)oxy]ethyl-benzenemethanaminium chloride may be used.

As the coumarin-based UV initiator, only one or a mixture of two or more selected from coumarin 1, coumarin 2, coumarin 6, coumarin 7, coumarin 30, coumarin 102, coumarin 106, coumarin 138, coumarin 152, coumarin 153, coumarin 307, coumarin 314, coumarin 314T, coumarin 334, coumarin 337, coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxycoumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, and 7-diethylamino-3-phenylcoumarin may be used.

As the thiazoline-based UV initiator, only one or a mixture of two or more selected from 3-(aroylmethylene)-thiazoline, 3-methyl-2-benzoylmethylene-β-naphthothiazoline, 3-methyl-2-benzoylmethylene-benzothiazoline, and 3-ethyl-2-propionylmethylene-β-naphtholthiazoline may be used.

As the rhodanine-based UV initiator, only one or a mixture of two or more selected from 4-dimethylaminobenzalrhodanine, 4-diethylaminobenzalrhodanine, and 3-ethyl-5-(3-octyl-2-benzothiazolinylidene)-rhodanine may be used.

In addition, as the other UV initiators, only one or a mixture of two or more selected from acetophenone, 3-methoxyacetophenone, 4-phenylacetophenone, α-dimethoxy-α-phenylacetophenone, hydroxy dimethyl acetophenone, benzyl, 4,4'-bis(dimethylamino)benzyl, methylbenzoylformate, diphenyl (2,4,6-trimethylbenzoyl)-phosphine oxide, phenyl bis(2,4,6-trimethyl benzoyl), oxy-phenyl-acetic acid-2-[2-oxo-2-phenyl-acetoxy-ethoxy]-ethyl ester, oxy-phenyl-acetic acid-2-[2-hydroxy-ethoxy]-ethyl ester, 4-cyclopentadiene-1-yl) bis[2,6-difluoro-3-(1-H-pyrrole-1-yl)phenyl] titanium, 2-acetylnaphthalene, 2-naphthalaldehyde, iodonium salt, dicylic acid derivatives, 9.10-anthraquinone, anthracene, pyrene, aminopyrene, perylene, phenanthrene, phenanthrenequinone, 9-fluorenone, dibenzosuberone, curcumin, xanthone, thiomichler's ketone, e.g., α-(4-dimethylaminobenzyllidene))ketone such as 2,5-bis(4-diethylaminobenzyllidene)cyclopentanone, 2-(4-dimethylamino-benzyllidene))-indan-1-one, or 3-(4-dimethylaminophenyl)-1-indan-5-yl-propenone, 3-phenylthiophthalimide, N-methyl-3,5-di(ethylthio)-phthalimide, N-methyl-3,5-di(ethylthio)-phthalimide, phenothiazine, methylphenothiazine, an amine such as, for example, N-phenylglycine, triethanolamine or N-methyldiethanolamine, ethyl-p-dimethylaminobenzoate, 2-(dimethylamino)ethylbenzoate, 2-ethylhexyl-p-dimethylaminobenzoate, octyl-para-N,N-dimethylaminobenzoate, N-(2-hydroxyethyl)-N-methyl-paratoluidine, butoxyethyl 4-dimethylaminobenzoate, 4-dimethylaminoacetophenone, triethanolamine, methyldiethanolamine, dimethylaminoethanol, 2-(dimethylamino)ethyl benzoate, polypropylene glycol)-4-(dimethylamino)benzoate, and michler's ketone may be used.

The UV crosslinking agent of the hydrogel resin ingredients used in the first step serves to adjust a crosslinking degree of a hydrogel to control adhesion and elasticity of the hydrogel. The content of the UV crosslinking agent may be 0.01 to 2% by weight, preferably 0.025 to 2% by weight, more preferably 0.025 to 1.5% by weight, based on a total weight of the hydrogel resin. When the content of the UV crosslinking agent is less than 0.01% by weight, a UV-cured hydrogel may exhibit too low viscoelasticity. On the other hand, when the content of the UV crosslinking agent is greater than 2% by weight, adhesion may be rather decreased.

In addition, as the UV crosslinking agent, only one or a mixture of two or more selected from benzyl methacrylate, lauryl methacrylate, isodecyl methacrylate, phenoxy methacrylate, 2-hydroxyethyl methacrylate, tetrahydro furfuryl methacrylate, cetyl(C16) methacrylate, stearyl methacrylate, methoxyPEG500 methacrylate, methoxyPEG600 methacrylate, methoxyPEG1000 methacrylate, 1,6-hexandiol dimethacrylate, butadiene dimethacrylate, neopentylglycol dimethacrylate, ethyleneglycol dimethacrylate, diethyleneglycol dimethacrylate, triethyleneglycol dimethacrylate, tetraethyleneglycol dimethacrylate, bisphenol A(EO)4 dimethacrylate, bisphenol A(EO)3 dimethacrylate, bisphenol A(EO)10 dimethacrylate, bisphenol A(EO)30 dimethacrylate, 1,3-butyleneglycol dimethacrylate, polyethylene glycol 400 dimethacrylate, polyethylene glycol 200 dimethacrylate, PPG1000(EO)15 dimethacrylate, PPG1000(EO)3 dimethacrylate, trimethylolpropane trimethacrylate, benzyl acrylate, lauryl acrylate, isodecyl acrylate, phenol(EO) acrylate, phenol(EO)2 acrylate, phenol(EO)4 acrylate, phenol(EO)6 acrylate, tetrahydro furfuryl acrylate, nonyl phenol(EO)4 acrylate, nonyl phenol(EO)8 acrylate, nonyl phenol(EO)2 acrylate, ethoxyethoxy ethyl acrylate, stearyl acrylate, 1,6-hexandiol diacrylate, 1,6-hexandiol(EO) diacrylate, butanediol diacrylate, hydroxy pivalic acid neopentyl glycol diacrylate, tripropylene glycol diacrylate, dipropylene glycol diacrylate, bisphenol A(EO)4 diacrylate, bisphenol A(EO)3 diacrylate, tricyclodecane dimethanol diacrylate, tetraethylene glycol diacrylate, polyethylene glycol 400 diacrylate, polyethylene glycol 200 diacrylate, polyethylene glycol 300 diacrylate, polyethylene glycol 600 diacrylate, polypropylene glycol 400 diacrylate, polypropylene glycol 750 diacrylate, bisphenol A(EO)10 diacrylate, bisphenol A(EO)30 diacrylate, tris(2-hydroxy ethyl)isocyanurate diacrylate, trimethylolpropane triacrylate, trimethylolpropane(EO)3 triacrylate, trimethylolpropane(EO)6 triacrylate, trimethylolpropane(EO)9 triacrylate, trimethylolpropane(EO)15 triacrylate, glycerin propoxylated triacrylate, pentaerythritol triacrylate, trimethylolpropane(PO)3 triacrylate, tris(2-hydroxy ethyl)isocyanurate triacrylate, pentaerythritol n-EO tetraacrylate, pentaerythritol tetraacrylate, dipentaerythritol pentaacrylate, dipentaerythritol hexaacrylate, caprolactone acrylate, O-phenylphenol EO acrylate, and methylene bisacrylamide may be used. Preferably, only one or a mixture of two or more selected from methylene bisacrylamide, 2-hydroxyethyl methacrylate, ethyleneglycol dimethacrylate, 1,3-butyleneglycol dimethacrylate, polyethyleneglycol 400 dimethacrylate, tripropyleneglycol diacrylate, and tetraethyleneglycol diacrylate may be used.

The second step of the method of preparing a cataplasm according to the present invention is a process of coating (or spreading) the hydrogel resin, which has been prepared in the first step, on a peel film. This coating may be performed by a general method used in the art.

In addition, the peel film is separated from a cataplasm immediately before attaching the cataplasm to the skin such that a drug layer is attached to the skin. An average thickness of the peel film (peel layer) is advantageously 15 μm to 500 μm, preferably 20 μm to 300 μm, in terms of easy peeling or ease of production.

In addition, the peel film is a polymer film coated with a silicone resin or a fluorine resin. The polymer film may include only one polymer compound or a mixture of two or more polymer compounds selected from polyester; polyvinyl chloride; polyvinylidenechloride; polyethyleneterephthalate; and a copolymer thereof.

The third step of the method of preparing a cataplasm of the present invention is a process of stacking a support on the hydrogel resin that is coated on the peel film. The support functions as a drug support layer of a cataplasm. As the support, only one or a mixture of two or more selected from a polyurethane film, a porous film, a perforated film, a fabric, a nonwoven fabric, and a foam may be used. In addition, the support may have an average thickness of 7 μm to 500 μm, preferably 50 μm to 250 μm. When the average thickness of the support is less than 7 μm, sufficient mechanical properties might not be secured due to too thin thickness, whereby the support might not function as a support for a hardened hydrogel (drug layer). When the average thickness of the support is greater than 500 μm, wearability may be decreased due to excessive thickness. Therefore, it is preferred to use a support having a thickness within the range.

The fourth step of the method of preparing a cataplasm of the present invention is a process of stacking a peel film, a hydrogel resin coating layer, and a support and then irradiating the support with UV to harden the hydrogel resin between the peel film and the support, thereby forming a hydrogel (drug layer). Here, the UV irradiation may be performed at an intensity of 2,000 to 8,000 mW/cm$^2$ for 3 to 10 minutes, preferably at 2,500 to 5,000 mW/cm$^2$ for 3 to 10 minutes.

An average thickness of the UV-hardened hydrogel is not specifically limited and may be preferably 20 μm to 2,000 μm, more preferably 40 μm to 1,000 μm.

In addition, a cumulative skin permeation rate of the active ingredient of the UV-hardened hydrogel, which is measured at 30 to 33° C. under a sink condition using a Franz diffusion cell having an effective area of 0.64 cm$^2$ and an aqueous phase volume of 5.2 ml, may be 40 to 160 μg/cm$^2$, preferably 45 to 150 μg/cm$^2$, more preferably 50 to 150 μg/cm$^2$.

In addition, a skin permeation speed of the active ingredient of the UV-hardened hydrogel, which is measured at 30 to 33° C. under a sink condition using a Franz diffusion cell having an effective area of 0.64 cm$^2$ and an aqueous phase volume of 5.2 ml, may be 1.0 to 7.5 μg/cm$^2$/hr, preferably 1.0 to 7.0 μg/cm$^2$/hr, more preferably 1.0 to 6.8 μg/cm$^2$/hr. Therefore, the UV-hardened hydrogel may have an excellent skin permeation speed.

In addition, the UV-hardened hydrogel, which is subjected to a peel strength test according to an adhesion test of the bandage section of the Korean Pharmacopoeia, may exhibits an adhesion of 40 gf to 150 gf, preferably 50 gf to 150 gf, more preferably 60 gf to 150 gf. Therefore, the UV-hardened hydrogel may have excellent adhesion to the skin.

A cataplasm prepared according to the method of the present invention includes a peel layer; a drug layer including a UV-curable hydrogel for transdermal administration; and a drug support layer. Here, the peel layer is the aforementioned peel film, and is removed upon application of the cataplasm to the skin. In addition, the drug support layer corresponds to the aforementioned support.

Particular use of the cataplasm of the present invention may depend upon an active ingredient in the drug layer. For example, a cataplasm for anti-inflammation or analgesic effects may be prepared upon use of lidocaine, lidocaine hydrochloride, loxoprofen, loxoprofenate, or the like as the active ingredient.

Hereinafter, the present invention will be described in more detail with reference to the following examples. However, the scope of the present invention is not limited to the ranges exemplified by the following examples.

EXAMPLE

Example 1

Preparation of Hydrogel Resin

A hydrogel resin was prepared by mixing, stirring, and completely dissolving 15% by weight of polyvinyl pyrrolidone, 0.25% by weight of flurbiprofen, 28.75% by weight of glycerin, 10% by weight of sorbitol, 15% by weight of propylene glycol, 0.01% by weight of 1-hydroxy-cyclohexyl-phenyl-ketone, 0.2% by weight of methylene bisacrylamide, and 30.79% by weight of purified water.

Examples 2 to 62

Hydrogel resins were prepared to have compositions and composition ratios summarized in Tables 1 to 7 below in the same manner as in Example 1.

TABLE 1

| Classification (% by weight) | | Examples | | | | | | | | | |
|---|---|---|---|---|---|---|---|---|---|---|---|
| | | 1 | 2 | 3 | 4 | 5 | 6 | 7 | 8 | 9 | 10 |
| Hydrophilic polymer | Polyvinyl pyrrolidone | 15 | 15 | 15 | 15 | 15 | 15 | 15 | 15 | 15 | 15 |
| Active ingredient | Flurbiprofen | 0.25 | 0.25 | 0.25 | 0.25 | 0.25 | 0.25 | 0.25 | 0.25 | 0.25 | 0.25 |
| Wetting agent | Glycerin | 28.75 | 28.75 | 28.75 | 28.75 | 28.75 | 28.75 | 28.75 | 28.75 | 28.75 | 28.75 |
| | Sorbitol | 10 | 10 | 10 | 10 | 10 | 10 | 10 | 10 | 10 | 10 |
| Transdermal penetration facilitator | Propylene glycol | 15 | 15 | 15 | 15 | 15 | 15 | 15 | 15 | 15 | 15 |
| Solvent | Purified water | 30.79 | 30.7 | 29.8 | 30.79 | 30.7 | 29.8 | 30.3 | 29.8 | 30.3 | 29.8 |
| UV initiator | 1-hydroxy-cyclohexyl-phenyl-ketone | 0.01 | 0.1 | 1 | — | — | — | — | — | — | — |
| | Benzophenone | — | — | — | 0.01 | 0.1 | 1 | — | — | — | — |
| | Methylbenzoylformate | — | — | — | — | — | — | 0.5 | 1 | — | — |
| | Phosphine oxide, phenyl bis(2,4,6-trimethylbenzoyl) | — | — | — | — | — | — | — | — | 0.5 | 1 |
| | 2-hydroxy-2-methyl-1-phenyl-1-propanone | — | — | — | — | — | — | — | — | — | — |
| UV crosslinking agent | Methylene bisacrylamide | 0.2 | 0.2 | 0.2 | 0.2 | 0.2 | 0.2 | 0.2 | 0.2 | 0.2 | 0.2 |

TABLE 2

| Classification (% by weight) | | Examples | | | | | | | | | |
|---|---|---|---|---|---|---|---|---|---|---|---|
| | | 11 | 12 | 13 | 14 | 15 | 16 | 17 | 18 | 19 | 20 |
| Hydrophilic polymer | Polyvinyl pyrrolidone | 15 | 15 | 15 | 15 | 10 | 20 | 15 | 15 | 15 | 15 |
| Active ingredient | Flurbiprofen | 0.25 | 0.25 | 0.25 | 0.25 | 0.25 | 0.25 | 0.25 | 0.25 | 0.25 | 0.25 |
| Wetting agent | Glycerin | 28.75 | 28.75 | 28.75 | 28.75 | 28.75 | 28.75 | 38.75 | 78.75 | 28.75 | 28.75 |
| | Sorbitol | 10 | 10 | 10 | 10 | 10 | 10 | 10 | 10 | 10 | 10 |
| Transdermal penetration facilitator | Propylene glycol | 15 | 15 | 15 | 15 | 15 | 15 | 15 | 15 | 15 | 15 |
| Solvent | Purified water | 30.3 | 29.8 | 30.6 | 29.8 | 35.6 | 25.6 | 20.6 | 40.6 | 30.5 | 30.7 |
| UV initiator | 1-hydroxy-cyclohexyl-phenyl-ketone | — | — | 0.1 | 0.5 | 0.1 | 0.1 | 0.1 | 0.1 | 0.1 | 0.1 |
| | Benzophenone | — | — | 0.1 | 0.5 | 0.1 | 0.1 | 0.1 | 0.1 | 0.1 | 0.1 |
| | Methylbenzoylformate | — | — | — | — | — | — | — | — | — | — |
| | Phosphine oxide, phenyl bis(2,4,6-trimethylbenzoyl) | — | — | — | — | — | — | — | — | — | — |
| | 2-hydroxy-2-methyl-1-phenyl-1-propanone | 0.5 | 1 | — | — | — | — | — | — | — | — |
| UV crosslinking agent | Methylene bisacrylamide | 0.2 | 0.2 | 0.2 | 0.2 | 0.2 | 0.2 | 0.2 | 0.2 | 0.3 | 0.1 |

TABLE 3

| Classification (% by weight) | | Examples | | | | | | | | | |
|---|---|---|---|---|---|---|---|---|---|---|---|
| | | 21 | 22 | 23 | 24 | 25 | 26 | 27 | 28 | 29 | 30 |
| Hydrophilic polymer | Polyvinyl pyrrolidone | 15 | 15 | 15 | 15 | 15 | 15 | 15 | 15 | 15 | 15 |
| Active ingredient | Flurbiprofen | 0.25 | 0.25 | 0.25 | 0.25 | 0.25 | 0.25 | 0.25 | 0.25 | 0.25 | 0.25 |
| Wetting agent | Glycerin | 25 | 25 | 25 | 25 | 25 | 25 | 25 | 25 | 25 | 25 |
| | Sorbitol | 13.75 | 13.75 | 13.75 | 13.75 | 13.75 | 13.75 | 13.75 | 13.75 | 13.75 | 13.75 |
| Transdermal penetration facilitator | Propylene glycol | 15 | 15 | 15 | 15 | 15 | 15 | 15 | 15 | 15 | 15 |
| Solvent | Purified water | 30.8 | 30.35 | 29.85 | 28.85 | 30.8 | 29.85 | 28.85 | 30.6 | 30.8 | 29.85 |
| UV initiator | Benzophenone | 0.15 | 0.15 | 0.15 | 0.15 | 0.15 | 0.15 | 0.15 | 0.15 | 0.15 | 0.15 |
| UV crosslinking agent | Methylene bisacrylamide | 0.05 | 0.5 | 1 | 2 | — | — | — | — | — | — |
| | 2-hydroxyethyl methacrylate | — | — | — | — | 0.05 | 1 | 2 | — | — | — |
| | Ethyleneglycol dimethacrylate | — | — | — | — | — | — | — | 0.25 | 0.05 | 1 |
| | 1,3-butyleneglycol dimethacrylate | — | — | — | — | — | — | — | — | — | — |
| | Polyethylene glycol 400 dimethacrylate | — | — | — | — | — | — | — | — | — | — |
| | Tripropyleneglycol diacrylate | — | — | — | — | — | — | — | — | — | — |
| | Tetraethyleneglycol diacrylate | — | — | — | — | — | — | — | — | — | — |

TABLE 4

| Classification (% by weight) | | \multicolumn{11}{c}{Examples} | | | | | | | | | | |
|---|---|---|---|---|---|---|---|---|---|---|---|
| | | 31 | 32 | 33 | 34 | 35 | 36 | 37 | 38 | 39 | 40 | 41 |
| Hydrophilic polymer | Polyvinyl pyrrolidone | 15 | 15 | 15 | 15 | 15 | 15 | 15 | 15 | 15 | 15 | 15 |
| Active ingredient | Lidocaine | 0.25 | 0.25 | 0.25 | 0.25 | 0.25 | 0.25 | 0.25 | 0.25 | 0.25 | 0.25 | 0.25 |
| Wetting agent | Glycerin | 25 | 25 | 25 | 25 | 25 | 25 | 25 | 25 | 25 | 25 | 25 |
| | Sorbitol | 13.75 | 13.75 | 13.75 | 13.75 | 13.75 | 13.75 | 13.75 | 13.75 | 13.75 | 13.75 | 13.75 |
| Transdermal penetration facilitator | Propylene glycol | 15 | 15 | 15 | 15 | 15 | 15 | 15 | 15 | 15 | 15 | 15 |
| Solvent | Purified water | 29.35 | 28.85 | 30.8 | 29.85 | 28.85 | 30.8 | 29.85 | 28.85 | 30.8 | 29.85 | 28.85 |
| UV initiator | Benzophenone | 0.15 | 0.15 | 0.15 | 0.15 | 0.15 | 0.15 | 0.15 | 0.15 | 0.15 | 0.15 | 0.15 |
| UV crosslinking agent | Methylene bisacrylamide | — | — | — | — | — | — | — | — | — | — | — |
| | 2-hydroxyethyl methacrylate | — | — | — | — | — | — | — | — | — | — | — |
| | Ethyleneglycol dimethacrylate | — | — | — | — | — | — | — | — | — | — | — |
| | 1,3-butyleneglycol dimethacrylate | 1.5 | 2 | — | — | — | — | — | — | — | — | — |
| | Polyethylene glycol 400 dimethacrylate | — | — | 0.05 | 1 | 2 | — | — | — | — | — | — |
| | Tripropylene glycol diacrylate | — | — | — | — | — | 0.05 | 1 | 2 | — | — | — |
| | Tetraethyleneglycol diacrylate | — | — | — | — | — | — | — | — | 0.05 | 1 | 2 |

TABLE 5

| Classification (% by weight) | | \multicolumn{6}{c}{Examples} | | | | | |
|---|---|---|---|---|---|---|---|
| | | 42 | 43 | 44 | 45 | 46 | 47 |
| Hydrophilic polymer | Polyvinyl pyrrolidone | 4 | 7 | 10 | 15 | 20 | 25 |
| Active ingredient | Flurbiprofen | 0.25 | 0.25 | 0.25 | 0.25 | 0.25 | 0.25 |
| Wetting agent | Glycerin | 25 | 25 | 25 | 15 | 10 | 5 |
| | Sorbitol | 13.75 | 13.75 | 13.75 | 13.75 | 13.75 | 8.75 |
| Transdermal penetration facilitator | Propylene glycol | 15 | 15 | 15 | 10 | 10 | 10 |
| Solvent | Purified water | 41.5 | 38.5 | 35.5 | 45.5 | 45.5 | 50.5 |
| UV initiator | Benzophenone | 0.15 | 0.15 | 0.15 | 0.15 | 0.15 | 0.15 |
| UV crosslinking agent | Methylene bisacrylamide | 0.25 | 0.25 | 0.25 | 0.25 | 0.25 | 0.25 |
| pH regulator | Tartaric acid | 0.1 | 0.1 | 0.1 | 0.1 | 0.1 | 0.1 |

TABLE 6

| Classification (% by weight) | | \multicolumn{9}{c}{Examples} | | | | | | | | |
|---|---|---|---|---|---|---|---|---|---|---|
| | | 48 | 49 | 50 | 51 | 52 | 53 | 54 | 55 | 56 |
| Hydrophilic polymer | Polyvinyl pyrrolidone | 10 | 10 | 10 | 10 | 10 | 10 | 10 | 10 | 10 |
| | Polyacrylic acid | 1 | 3 | 5 | 0 | 0 | 0 | 0 | 0 | 0 |
| | Polyacrylamide | 0 | 0 | 0 | 1 | 3 | 5 | 0 | 0 | 0 |
| | Hydroxypropyl cellulose | 0 | 0 | 0 | 0 | 0 | 0 | 1 | 3 | 5 |
| Active ingredient | Flurbiprofen | 0.25 | 0.25 | 0.25 | 0.25 | 0.25 | 0.25 | 0.25 | 0.25 | 0.25 |
| Wetting agent | Glycerin | 15 | 10 | 10 | 15 | 10 | 10 | 15 | 10 | 10 |
| | Sorbitol | 13.75 | 13.75 | 8.75 | 13.75 | 13.75 | 8.75 | 13.75 | 13.75 | 8.75 |

TABLE 6-continued

|  | Classification (% by weight) | Examples | | | | | | | | |
| --- | --- | --- | --- | --- | --- | --- | --- | --- | --- | --- |
|  |  | 48 | 49 | 50 | 51 | 52 | 53 | 54 | 55 | 56 |
| Transdermal penetration facilitator | Propylene glycol | 15 | 10 | 10 | 15 | 10 | 10 | 15 | 10 | 10 |
| Solvent | Purified water | 44.6 | 52.6 | 55.6 | 44.6 | 52.6 | 55.6 | 44.6 | 52.6 | 55.6 |
| UV initiator | Benzophenone | 0.15 | 0.15 | 0.15 | 0.15 | 0.15 | 0.15 | 0.15 | 0.15 | 0.15 |
| UV crosslinking agent | Ethyleneglycol dimethacrylate | 0.25 | 0.25 | 0.25 | 0.25 | 0.25 | 0.25 | 0.25 | 0.25 | 0.25 |

TABLE 7

|  | Classification (% by weight) | Examples | | | | | |
| --- | --- | --- | --- | --- | --- | --- | --- |
|  |  | 57 | 58 | 59 | 60 | 61 | 62 |
| Hydrophilic polymer | Polyvinyl pyrrolidone | 15 | 15 | 15 | 15 | 15 | 15 |
| Active ingredient | Flurbiprofen | 0.25 | 0.25 | 0.25 | 0.25 | 0.25 | 0.25 |
| Wetting agent | Glycerin | 25 | 25 | 25 | 25 | 25 | 25 |
|  | Sorbitol | 13.75 | 13.75 | 13.75 | 13.75 | 13.75 | 13.75 |
| Transdermal penetration facilitator | Propylene glycol | 15 | 15 | 15 | 15 | 15 | 15 |
|  | Sorbitanmonooleate | 1 | — | — | — | — | — |
|  | Isopropylmyristate | — | 1 | — | — | — | — |
|  | Polyoxyethylene monooleate | — | — | 1 | — | — | — |
|  | Glycerolmonooleate | — | — | — | 1 | — | — |
|  | Propyleneglycolmonolaurate | — | — | — | — | 1 | — |
|  | Polyglyceryl diisostearate | — | — | — | — | — | 1 |
| Solvent | Purified water | 29.6 | 29.6 | 29.6 | 29.6 | 29.6 | 29.6 |
| UV initiator | Benzophenone | 0.15 | 0.15 | 0.15 | 0.15 | 0.15 | 0.15 |
| UV crosslinking agent | Methylene bisacrylamide | 0.25 | 0.25 | 0.25 | 0.25 | 0.25 | 0.25 |

Examples 63 to 70

Hydrogel resins were prepared to have compositions and composition ratios of Table 8 in the same manner as in Example 1 except that a different active ingredient was used.

TABLE 8

|  | Classification (% by weight) | Examples | | | | | | | |
| --- | --- | --- | --- | --- | --- | --- | --- | --- | --- |
|  |  | 63 | 64 | 65 | 66 | 67 | 68 | 69 | 70 |
| Hydrophilic polymer | Polyvinyl pyrrolidone | 15 | 15 | 15 | 15 | 15 | 15 | 15 | 15 |
| Active ingredient | Loxoprofen sodium | 1.5 | 1.5 | 1.5 | 1.5 | 1.5 | 1.5 | 1.5 | 2 |
| Wetting agent | Glycerin | 28 | 28 | 28 | 28 | 28 | 28 | 28 | 33 |
|  | Sorbitol | 7 | 7 | 7 | 7 | 7 | 7 | 7 | 5 |
| Transdermal penetration facilitator | Triacetin | — | — | 2 | — | 2 | 1.5 | — | — |
|  | Propylene glycol | 28 | 28 | 28 | 28 | 28 | 28 | 28 | 28.53 |
|  | Glycerin monooleate | 2 | — | — | — | — | — | 1 | 1 |
|  | N-methyl-2-pyrrolidone (NMP) | 0.3 | 0.3 | 0.3 | 0.3 | 0.3 | 0.3 | 0.3 | 0.3 |
|  | Polyoxyethylene sorbitan | 0.4 | 0.4 | 0.4 | 0.4 | 0.4 | 0.4 | 0.4 | 0.2 |
|  | Lauryl pyrrolidone | — | 2 | — | — | 1 | 1.5 | 1 | 1 |
| Solvent | Purified water | 16.78 | 16.78 | 16.78 | 16.78 | 16.78 | 16.78 | 16.78 | 13 |
| UV initiator | Benzophenone | 0.11 | 0.11 | 0.11 | 0.11 | 0.11 | 0.11 | 0.11 | 0.1 |
| UV crosslinking agent | Glycol HEMA-methacrylate | 0.16 | 0.16 | 0.16 | 0.16 | 0.16 | 0.16 | 0.16 | 0.15 |

TABLE 8-continued

|  |  | Examples | | | | | | | |
| --- | --- | --- | --- | --- | --- | --- | --- | --- | --- |
| Classification (% by weight) | | 63 | 64 | 65 | 66 | 67 | 68 | 69 | 70 |
| pH regulator | Tartaric acid | 0.1 | 0.1 | 0.1 | 0.1 | 0.1 | 0.1 | 0.1 | 0.1 |
| Preservative | Methylparaben | 0.15 | 0.15 | 0.15 | 0.15 | 0.15 | 0.15 | 0.15 | 0.12 |
| Flavoring agent | L-menthol | 0.5 | 0.5 | 0.5 | 0.5 | 0.5 | 0.5 | 0.5 | 0.5 |

Examples 71 to 74

Hydrogel resins were prepared to have compositions and composition ratios of Table 9 in the same manner as in Example 1 except that different active ingredient was used.

TABLE 9

|  |  | Examples | | | |
| --- | --- | --- | --- | --- | --- |
| Classification (% by weight) | | 71 | 72 | 73 | 74 |
| Hydrophilic polymer | Polyvinyl pyrrolidone | 10 | 10 | 10 | 10 |
| Active ingredient | Flurbiprofen | 1 | 1 | 1.2 | 1.2 |
| Wetting agent | Glycerin | 30 | 31 | 31 | 30 |
|  | Sorbitol | 10 | 10 | 10 | 10 |
| Transdermal penetration facilitator | Propylene glycol | 23 | 23 | 23 | 23 |
|  | Sorbitanmonooleate | 1 | 1 | 1 | 1 |
|  | Lauryl pyrrolidone | 1 | 1 | 1 | 1 |
| Solvent | Purified water | 22.63 | 21.68 | 21.5 | 22.53 |
| UV initiator | Benzophenone | 0.12 | 0.07 | 0.05 | 0.02 |
| UV crosslinking agent | Glycol HEMA-methacrylate | 0.25 | 0.25 | 0.25 | 0.25 |
| Flavoring agent | Menthol | 1 | 1 | 1 | 1 |

TABLE 10

| Classification (% by weight) | Comparative Example 1 |
| --- | --- |
| Flurbiprofen | 0.5 |
| Glycerin | 19.00 |
| Sorbitol | 20.00 |
| Polyacrylate solution | 10.00 |
| Sodium polyacrylate | 5.00 |
| Sodium carboxymethyl cellulose | 5.00 |
| Propylene glycol | 5.00 |
| Urea | 3.00 |
| Tartaric acid | 1.50 |
| Dihydroxy aluminum aminoacetate | 0.25 |
| Purified water | 30.75 |

Comparative Examples 2 to 10

Hydrogel resins were prepared to have compositions and composition ratios of Table 11 below in the same manner as in Example 1.

TABLE 11

|  |  | Comparative Examples | | | | | | |
| --- | --- | --- | --- | --- | --- | --- | --- | --- |
| Classification | | 2 | 3 | 4 | 5 | 6 | 7 | 8 |
| Hydrophilic polymer | Polyvinyl pyrrolidone | 3 | 65 | 15 | 20 | 17 | 15 | 15 |
| Active ingredient | Flurbiprofen | 4 | 4 | 17 | 5 | 5 | 4 | 4 |
| Wetting agent | Glycerin | 25 | 10 | 25 | 0.2 | 25 | 25 | 25 |
|  | Sorbitol | 10 | 5 | 10 | 0.2 | 10 | 10 | 10 |
| Transdermal penetration facilitator | Lauryl pyrrolidone | 15 | 10 | 15 | 30 | 0 | 15 | 15 |
| Solvent | Purified water | 44.6 | 5.6 | 17.6 | 44.2 | 42.6 | 30.75 | 30.85 |
| UV initiator | 1-hydroxy-cyclohexyl-phenyl-ketone | 0.15 | 0.15 | 0.15 | 0.15 | 0.15 | 0 | 0.15 |
| UV crosslinking agent | Methylene bisacrylamide | 0.25 | 0.25 | 0.25 | 0.25 | 0.25 | 0.25 | 0 |

Comparative Example 1

A hydrogel resin was prepared to have a composition and a composition ratio summarized in Table 10 below. A hydrogel resin having the composition of Table 10 below was hardened by metal complex ion crosslinking. A hardening time of the hydrogel resin was 14 days.

Preparation Example 1

Preparation of Cataplasm

The hydrogel solution prepared in Example 1 was coated on one surface of a polyester film (thickness: 75 μm) coated with a silicone resin. The hydrogel resin coating layer was covered with a nonwoven fabric, and then hardened by UV-irradiating for 4 minutes, thereby preparing a cataplasm in which a peel layer (peel film), a drug layer (hydrogel) and a drug support layer (nonwoven fabric) were stacked and integrated. The hydrogel was prepared to have an average thickness of 500 μm.

Preparation Examples 2 to 74 and Comparative Preparation Examples 2 to 10

Cataplasms of Preparation Examples 2 to 74 were prepared in the same manner as in Example 1, except that the hydrogel resins of Examples 2 to 74 were respectively used instead of the hydrogel resin of Example 1.

Comparative Preparation Example 1

A cataplasm was prepared in the same manner as in Example 1, except that hardening by metal complex ionic bonding, instead of UV irradiation, was performed by allowing to stand at room temperature (25° C. to 27° C.) for 14 days. In addition, hardening was determined by whether the hydrogel was smeared and the hydrogel was stained on the nonwoven fabric.

Comparative Preparation Examples 2 to 8

Cataplasms of Comparative Preparation Examples 2 to 8 were prepared in the same manner as in Example 1, except that the hydrogel resins of Comparative Examples 2 to 8 were used instead of the hydrogel resins of Example 1.

Experimental Example 1

Adhesion Measurement

To investigate adhesion of the cataplasms prepared according to the preparation examples and the comparative preparation examples, 180° peel tests were performed. Results are shown in Tables 12 and 13 below. Adhesion was measured as follows: the peel layer was removed from the cataplasm, and then the cataplasm was cut into a size of a standard width of 12 mm and a length of 250 mm and was attached to a test plate with a width 12 mm and a length of 125 mm made of a phenol resin. A rubber roller with a mass of 850 g was rolled on the cataplasm twice at a speed of 300 mm for 1 minute such that the cataplasm was tightly attached to the test plate. Subsequently, the test plate was pulled out at a speed of 300 mm using a tensile strength tester (Instron 5544), and the load was measured four times at intervals of about 20 mm.

TABLE 12

| Classification | Adhesion (gf) |
| --- | --- |
| Preparation Example 1 | 70 |
| Preparation Example 2 | 64 |
| Preparation Example 3 | 61 |
| Preparation Example 4 | 71 |
| Preparation Example 5 | 64 |
| Preparation Example 6 | 60 |
| Preparation Example 7 | 71 |
| Preparation Example 8 | 63 |

TABLE 12-continued

| Classification | Adhesion (gf) |
| --- | --- |
| Preparation Example 9 | 68 |
| Preparation Example 10 | 61 |
| Preparation Example 11 | 72 |
| Preparation Example 12 | 61 |
| Preparation Example 13 | 81 |
| Preparation Example 14 | 68 |
| Preparation Example 15 | 62 |
| Preparation Example 16 | 95 |
| Preparation Example 17 | 85 |
| Preparation Example 18 | 69 |
| Preparation Example 19 | 79 |
| Preparation Example 20 | 76 |
| Preparation Example 21 | 68 |
| Preparation Example 22 | 64 |
| Preparation Example 23 | 63 |
| Preparation Example 24 | 61 |
| Preparation Example 25 | 58 |
| Preparation Example 26 | 58 |
| Preparation Example 27 | 57 |
| Preparation Example 28 | 60 |
| Preparation Example 29 | 65 |
| Preparation Example 30 | 68 |
| Preparation Example 31 | 60 |
| Preparation Example 32 | 58 |
| Preparation Example 33 | 65 |
| Preparation Example 34 | 62 |
| Preparation Example 35 | 60 |
| Preparation Example 36 | 68 |
| Preparation Example 37 | 63 |
| Preparation Example 38 | 61 |
| Preparation Example 39 | 63 |
| Preparation Example 40 | 62 |
| Preparation Example 41 | 64 |
| Preparation Example 42 | 53 |
| Preparation Example 43 | 55 |
| Preparation Example 44 | 56 |
| Preparation Example 45 | 62 |
| Preparation Example 46 | 65 |
| Preparation Example 47 | 68 |

TABLE 12-continued

| Classification | Adhesion (gf) |
| --- | --- |
| Preparation Example 48 | 56 |
| Preparation Example 49 | 58 |
| Preparation Example 50 | 63 |
| Preparation Example 51 | 56 |
| Preparation Example 52 | 57 |
| Preparation Example 53 | 55 |
| Preparation Example 54 | 58 |
| Preparation Example 55 | 57 |
| Preparation Example 56 | 61 |
| Preparation Example 57 | 63 |
| Preparation Example 58 | 64 |
| Preparation Example 59 | 63 |
| Preparation Example 60 | 61 |
| Preparation Example 61 | 60 |
| Preparation Example 62 | 63 |
| Preparation Example 63 | 70 |
| Preparation Example 64 | 71 |
| Preparation Example 65 | 73 |
| Preparation Example 66 | 71 |
| Preparation Example 67 | 72 |
| Preparation Example 68 | 68 |
| Preparation Example 69 | 67 |
| Preparation Example 70 | 70 |
| Preparation Example 71 | 65 |
| Preparation Example 72 | 67 |
| Preparation Example 73 | 69 |
| Preparation Example 74 | 68 |

TABLE 13

| Classification | Adhesion (gf) |
| --- | --- |
| Comparative Preparation Example 1 | 38 |
| Comparative Preparation Example 2 | x |
| Comparative Preparation Example 3 | 58 |
| Comparative Preparation Example 4 | 37 |
| Comparative Preparation Example 5 | 32 |
| Comparative Preparation Example 6 | 64 |
| Comparative Preparation Example 7 | x |
| Comparative Preparation Example 8 | x |

In the case of Comparative Example 2 using the hydrogel resin including less than 5% by weight of a hydrophilic polymer, Comparative Preparation Example 7 using the hydrogel resin excluding a UV initiator, and Comparative Preparation Example 8 using the hydrogel resin excluding a UV crosslinking agent, gel formation was not satisfactorily accomplished or crosslinking was not accomplished. Accordingly, it was impossible to measure adhesion.

In addition, in the case of Comparative Preparation Example 4 including greater than 15% by weight of the active ingredient, a low adhesion of 37 gf, less than 50 gf, was observed. This result may be interpreted as being due to the excessively used active ingredient interfering with crosslinking and thus causing adhesion decrease of the hydrogel.

Further, in the case of Comparative Preparation Example 5 including less than 0.6% by weight of the wetting agent, adhesion was very poor. This result may be interpreted as being due to excessive dryness of an attached portion of the UV-hardened hydrogel, which caused adhesion decrease.

Experimental Example 2

Measurement of Cumulative Skin Permeation Rate and Skin Permeation Speed

The active ingredient in the drug layer of the cataplasm prepared according to Preparation Examples 1 to 74 and Comparative Preparation Examples 1 and 3 to 6 was subjected to cumulative skin permeation rate and skin permeation speed measurement experiments.

A cumulative skin permeation rate was conducted under a sink condition under using a Franz diffusion cell (effective area: 0.64 cm$^2$, the volume of an aqueous phase: 5.2 ml). More particularly, a Franz diffusion cell was filled with aqueous phosphate buffered saline (PBS) at pH 7.4 and the temperature thereof was maintained at 32±0.5° C., and then a sample was cut into a circle shape (area: 0.64 cm$^2$) and was attached to the center of the prepared skin (human cadaver skin epidermis). The skin, to which the sample had been attached, was placed on the Franz diffusion cell, and then was covered with a doner and fixed with a clamp, followed by performing permeation experiments.

A human cadaver skin epidermis layer for experimentation was purchased, and was used as the skin sample. The purchased human cadaver skin epidermis layer was stored at −70° C., and was used after thawing at 40° C. Active ingredient permeation analysis was conducted for 24 hours using HPLC. Results are summarized in Tables 14 and 15 below.

TABLE 14

| Classification | Cumulative skin permeation rate ($\mu g/cm^2$) | Skin permeation speed ($\mu g/cm^2/hr$) |
| --- | --- | --- |
| Preparation Example 1 | 55 ± 5.70 | 2.292 |
| Preparation Example 2 | 53 ± 5.84 | 2.208 |

TABLE 14-continued

| Classification | Cumulative skin permeation rate (μg/cm²) | Skin permeation speed (μg/cm²/hr) |
| --- | --- | --- |
| Preparation Example 3 | 51 ± 1.51 | 2.125 |
| Preparation Example 4 | 48 ± 2.81 | 2.000 |
| Preparation Example 5 | 57 ± 5.1 | 2.375 |
| Preparation Example 6 | 58 ± 5.07 | 2.417 |
| Preparation Example 7 | 60 ± 7.09 | 2.500 |
| Preparation Example 8 | 63 ± 3.19 | 2.625 |
| Preparation Example 9 | 57 ± 5.7 | 2.375 |
| Preparation Example 10 | 49 ± 5.1 | 2.042 |
| Preparation Example 11 | 57 ± 4.3 | 2.375 |
| Preparation Example 12 | 56 ± 9.1 | 2.333 |
| Preparation Example 13 | 55 ± 7.5 | 2.208 |
| Preparation Example 14 | 67 ± 5.74 | 2.208 |
| Preparation Example 15 | 54 ± 2.21 | 2.208 |
| Preparation Example 16 | 56 ± 2.71 | 2.208 |
| Preparation Example 17 | 57 ± 7.27 | 2.208 |
| Preparation Example 18 | 55 ± 7.75 | 2.208 |
| Preparation Example 19 | 48 ± 3.28 | 2.208 |
| Preparation Example 20 | 57 ± 7.87 | 2.208 |
| Preparation Example 21 | 67 ± 5.63 | 2.792 |
| Preparation Example 22 | 51 ± 3.93 | 2.125 |
| Preparation Example 23 | 57 ± 7.51 | 2.375 |
| Preparation Example 24 | 54 ± 7.34 | 2.250 |
| Preparation Example 25 | 56 ± 4.57 | 2.333 |
| Preparation Example 26 | 57 ± 7.12 | 2.375 |
| Preparation Example 27 | 61 ± 2.78 | 2.542 |
| Preparation Example 28 | 57 ± 7.3 | 2.208 |
| Preparation Example 29 | 58 ± 10.1 | 2.417 |
| Preparation Example 30 | 59 ± 7.2 | 2.458 |
| Preparation Example 31 | 62 ± 7.99 | 2.583 |
| Preparation Example 32 | 55 ± 5.12 | 2.292 |
| Preparation Example 33 | 57 ± 6.78 | 2.375 |
| Preparation Example 34 | 51 ± 2.78 | 2.125 |
| Preparation Example 35 | 53 ± 7.18 | 2.208 |
| Preparation Example 36 | 57 ± 2.07 | 2.375 |
| Preparation Example 37 | 56 ± 4.27 | 2.333 |
| Preparation Example 38 | 57 ± 3.93 | 2.208 |
| Preparation Example 39 | 54 ± 5.24 | 2.208 |
| Preparation Example 40 | 57 ± 7.91 | 2.208 |
| Preparation Example 41 | 55 ± 5.17 | 2.208 |
| Preparation Example 42 | 61 ± 3.87 | 2.208 |
| Preparation Example 43 | 57 ± 4.93 | 2.208 |
| Preparation Example 44 | 51 ± 4.78 | 2.208 |
| Preparation Example 45 | 49 ± 5.89 | 2.208 |
| Preparation Example 46 | 58 ± 5.14 | 2.417 |
| Preparation Example 47 | 53 ± 7.79 | 2.208 |
| Preparation Example 48 | 52 ± 7.12 | 2.167 |
| Preparation Example 49 | 51 ± 8.17 | 2.125 |
| Preparation Example 50 | 54 ± 5.42 | 2.250 |
| Preparation Example 51 | 51 ± 2.1 | 2.125 |
| Preparation Example 52 | 52 ± 3.45 | 2.167 |
| Preparation Example 53 | 57 ± 4.12 | 2.208 |

TABLE 14-continued

| Classification | Cumulative skin permeation rate ($\mu g/cm^2$) | Skin permeation speed ($\mu g/cm^2/hr$) |
|---|---|---|
| Preparation Example 54 | 61 ± 3.78 | 2.542 |
| Preparation Example 55 | 57 ± 3.1 | 2.375 |
| Preparation Example 56 | 56 ± 7.12 | 2.333 |
| Preparation Example 57 | 72 ± 6.22 | 3.000 |
| Preparation Example 58 | 71 ± 5.81 | 2.958 |
| Preparation Example 59 | 75 ± 7.14 | 3.125 |
| Preparation Example 60 | 77 ± 7.37 | 3.208 |
| Preparation Example 61 | 81 ± 8.17 | 3.375 |
| Preparation Example 62 | 77 ± 7.57 | 3.208 |
| Preparation Example 63 | 94.96 ± 15.28 | 3.950 |
| Preparation Example 64 | 148 ± 9.03 | 6.610 |
| Preparation Example 65 | 51 ± 7.52 | 2.120 |
| Preparation Example 66 | 84.97 ± 2.32 | 3.540 |
| Preparation Example 67 | 84 ± 3.15 | 3.500 |
| Preparation Example 68 | 93 ± 4.55 | 3.875 |
| Preparation Example 69 | 81 ± 4.13 | 3.375 |
| Preparation Example 70 | 97 ± 17.13 | 4.040 |
| Preparation Example 71 | 81 ± 11.23 | 3.375 |
| Preparation Example 72 | 84 ± 9.12 | 3.500 |
| Preparation Example 73 | 86 ± 7.7 | 3.583 |
| Preparation Example 74 | 87 ± 3.14 | 3.625 |
| — | — | — |

TABLE 15

| Classification | Cumulative skin permeation rate ($\mu g/cm^2$) | Skin permeation speed ($\mu g/cm^2/hr$) |
|---|---|---|
| Comparative Preparation Example 1 | 6.28 ± 0.63 | 0.260 |
| Comparative Preparation Example 3 | 33 ± 1.52 | 1.181 |
| Comparative Preparation Example 4 | 79 ± 0.58 | 2.832 |
| Comparative Preparation Example 5 | 81 ± 1.13 | 3.375 |
| Comparative Preparation Example 6 | 12 ± 0.94 | 0.519 |

As shown in Table 13, it can be confirmed that the cataplasms of Preparation Examples 1 to 74 exhibit a cumulative skin permeation rate of 40 $\mu g/cm^2$ or more and a skin permeation speed of 2.0 $\mu g/cm^2/hr$ or more.

However, it can be confirmed that the conventional cataplasm of Comparative Preparation Example 1 prepared by metal complex ionic bonding exhibits a low cumulative skin permeation rate and a low skin permeation speed.

In addition, it can be confirmed that Comparative Preparation Example 3 including greater than 60% by weight of the hydrophilic polymer exhibits excellent adhesion as shown in Table 12, but exhibits a low cumulative skin permeation rate and a low skin permeation speed compared to the preparation examples of Table 13. These results may be interpreted as occurring because the large amount of hydrophilic polymer forming crosslinks in the hydrogel rather deteriorates the skin permeation ability of the active ingredient.

In addition, it can be confirmed that Comparative Preparation Example 4 including greater than 15% by weight of the active ingredient and Comparative Preparation Example 5 including less than 0.6% by weight of the wetting agent exhibit excellent cumulative skin permeation rate and skin permeation speed, but poor adhesion as shown in Table 12.

In addition, it can be confirmed that Comparative Preparation Example 6 excluding the transdermal penetration facilitator exhibits excellent adhesion, but very poor cumulative skin permeation rate and skin permeation speed.

From the results of the examples and experimental examples, it can be confirmed that the drug layer (hydrogel) in the cataplasm prepared using the hydrogel resin of the present invention has superior economic efficiency and marketability due to the high hardening speed thereof, excellent skin permeation ability and speed, and excellent adhesion to the skin. In addition, it is anticipated that the cataplasm of the present invention can be used to provide various pharmaceutical patches.

Simple variations or modifications of the present invention may be readily practiced by those skilled in the art and all such modifications and variations are intended to be included within the scope of the present invention.

The invention claimed is:

1. A UV-curable hydrogel resin for cataplasm, comprising 5 to 35% by weight of a hydrophilic polymer, 0.1 to 10% by weight of an active ingredient, 12 to 40% by weight of a wetting agent, 0.5 to 25% by weight of a transdermal penetration facilitator, 0.01 to 2.0% by weight of a UV initiator, and 0.01 to 2.0% by weight of a UV crosslinking agent, and the remaining amount of a solvent,
wherein the hydrophilic polymer comprises one or more selected from polyvinyl alcohol, polyvinyl pyrrolidone, a polyvinyl pyrrolidone/vinyl acetate copolymer, a vinyl ether/anhydric maleic acid copolymer, an isobutylene/anhydric maleic acid copolymer, a methoxyethylene/anhydric maleic acid copolymer, a methacrylic acid/butyl acrylate copolymer, alginate, hydroxyethyl methacrylate, hydroxyethyl cellulose, hydroxypropyl cellulose, hydroxypropyl methylcellulose, ethyl cellulose, methyl cellulose, sodium carboxymethyl cellulose, a carboxyvinyl copolymer, polyethylene oxide, polyethylene glycol, polyacrylamide, polyhydroxyethyl methacrylate, polydioxolane, polyacrylic acid, sodium polyacrylate, polyvinyl acrylate, polyacryl acetate, and polyvinyl chloride, wherein the active ingredient comprises one or more selected from lidocaine, lidocaine hydrochloride, loxoprofen, loxoprofenate, ketoprofen, flurbiprofen, diclofenac, diclofenac salt, indomethacin, piroxicam, meloxicam, naproxen, ibuprofen, felbinac, menthol, glycol salicylate, methyl salicylate, pepper extracts, vanillyl nonylamide, butyl vinyl ether, centella asiatica, fusidic acid, fusidate, acrinol, Pueraria mirifica, heparin, heparinate, and allantoin, wherein the transdermal penetration facilitator comprises one or more selected from propylene glycol, dipropylene glycol, polyoxyethylene monooleate, polyglyceryl diisostearate, glycerin monooleate, polyoxyethylene sorbitan, N-methyl-2-pyrrolidone, N-carprylyl-2-pyrrolidone, N-dodecyl-2-pyrrolidone, lauryl pyrrolidone, isopropyl myristrate, sorbitan mono-oleate, propylene monolaurate, glycerol monolaurate, glycerol monooleate, and triacetin, wherein the wetting agent comprises one or more selected from glycerin, and sorbitol.

2. The UV-curable hydrogel resin according to claim 1, wherein the UV initiator comprises one or more selected from a ketone-based UV initiator, a thioxantone-based UV initiator, a benzophenone-based UV initiator, a coumarin-based UV initiator, a thiazoline-based UV initiator, a rhodanine-based UV initiator, and other UV initiators, wherein the ketone-based UV initiator comprises one or more of 1-hydroxy-cyclohexyl-phenyl-ketone, 2-hydroxy-2-methyl-1-phenyl-1-propanone, 2-hydroxy-1-[4-(2-hydroxyethoxy)phenyl]-2-methyl-1-propanone, 2-benzyl-2-(dimethylamino)-1-[4-(4-morpholinyl)phenyl]-1-butanone, and 2-methyl-1-[4-(methylthio)phenyl]-2-(4-morpholinyl)-1-propanone, the thioxantone-based UV initiator comprises one or more of thioxanthone, 2-isopropylthioxanthone, 2-chlorothioxanthone, 1-chloro-4-propoxythioxanthone, 2-dodecylthioxanthone, 2,4-diethylthioxanthone, 2,4-dimethylthioxanthone, 1-methoxy-carbonylthioxanthone, 2-ethoxycarbonylthioxanthone, 3-(2-methoxyethoxycarbonyl)-thioxanthone, 4-butoxycarbonylthioxanthone, 3-butoxycarbonyl-7-methylthioxanthone, 1-cyano-3-chlorothioxanthone, 1-ethoxycarbonyl-3-chlorothioxanthone, 1-ethoxycarbonyl-3-ethoxythioxanthone, 1-ethoxycarbonyl-3-aminothioxanthone, 1-ethoxycarbonyl-3-phenylsulfurylthioxanthone, 3,4-di[2-(2-methoxyethoxy)ethoxycarbonyl]-thioxanthone, 1,3-dimethyl-3-hydroxy-9H-thioxanthone-9-one 2-eylhexylether, 1-ethoxycarbonyl-3-(1-methyl-1-morpholinoethyl)-thioxanthone, 2-methyl-6-dimethoxymethyl-thioxanthone, 2-methyl-6-(1,1-dimethoxybenzyl)-thioxanthone, 2-morpholinomethylthioxanthone, 2-methyl-6-morpholinomethylthioxanthone, N-allylthioxanthone-3,4-dicarboxamide, 1-phenoxythioxanthone, 6-ethoxycarbonyl-2-methoxythioxanthone, 6-ethoxycarbonyl-2-methylthioxanthone, thioxanthone-2-carboxylic acid polyethylene glycol ether, and 2-hydroxy-3-(3,4-dimethyl-9-oxo-9H-thioxanthone-2-2-yloxy)-N,N,N-trimethyl-1-propanaminiumchloride, the benzophenone-based UV initiator comprises one or more of benzophenone, 4-phenyl benzophenone, 4-methoxy benzophenone, 4,4'-dimethyl benzophenone, 4,4'-dichlorobenzophenone, 4,4'-bis(dimethylamino)-benzophenone, 4,4'-bis(diethylamino)benzophenone, 4,4'-bis(methylethylamino)benzophenone, 4,4'-bis(p-isopropylphenoxy)benzophenone, 3,3'-dimethyl-4-methoxy benzophenone, methyl-2-benzoylbenzoate, 4-(2-hydroxyethylthio)-benzophenone, 4-(4-tolylthio)benzophenone, 1-[4-4-benzoyl-phenylsulfanyl)-phenyl]-2-methyl-2(toluene-4-sulfonyl)-propane-1-one, 4-benzoyl-N,N,N-trimethylbenzenemethanaminium chloride, 2-hydroxy-3-(4-benzoyl-phenoxy)-N,N,N-trimethyl-1-propaneaminium chloride monohydrate, 4-(13-acryloyl-1,4,7,10,13-pentaoxatridecyl)-benzophenone, and 4-benzoyl-N,N-dimethyl-N-[2-(1-oxo-2-prophenyl)oxy]ethyl-benzenemethanaminium chloride, the coumarin-based UV initiator comprises one or more of coumarin 1, coumarin 2, coumarin 6, coumarin 7, coumarin 30, coumarin 102, coumarin 106, coumarin 138, coumarin 152, coumarin 153, coumarin 307, coumarin 314, coumarin 314T, coumarin 334, coumarin 337, coumarin 500, 3-benzoyl coumarin, 3-benzoyl-7-methoxycoumarin, 3-benzoyl-5,7-dimethoxycoumarin, 3-benzoyl-5,7-dipropoxycoumarin, 3-benzoyl-6,8-dichlorocoumarin, 3-benzoyl-6-chloro-coumarin, 3,3'-carbonyl-bis[5,7-di(propoxy)-coumarin], 3,3'-carbonyl-bis(7-methoxycoumarin), 3,3'-carbonyl-bis(7-diethylamino-coumarin), 3-isobutyroylcoumarin, 3-benzoyl-5,7-dimethoxy-coumarin, 3-benzoyl-5,7-diethoxy-coumarin, 3-benzoyl-5,7-dibutoxycoumarin, 3-benzoyl-5,7-di(methoxyethoxy)-coumarin, 3-benzoyl-5,7-di(allyloxy)coumarin, 3-benzoyl-7-dimethylaminocoumarin, 3-benzoyl-7-diethylaminocoumarin, 3-isobutyroyl-7-dimethylaminocoumarin, 3-benzoyl-7-diethylaminocoumarin, 3-isobutyroyl-7-dimethylaminocoumarin, 5,7-dimethoxy-3-(1-naphthoyl)-coumarin, 5,7-diethoxy-3-(1-naphthoyl)-coumarin, 3-benzoylbenzo[f]coumarin, 7-diethylamino-3-thienoylcoumarin, 3-(4-cyanobenzoyl)-5,7-dimethoxycoumarin, 3-(4-cyanobenzoyl)-5,7-dipropoxycoumarin, 7-dimethylamino-3-phenylcoumarin, and 7-diethylamino-3-phenylcoumarin, the thiazoline-based UV initiator comprises one or more of 3-(aroylmethylene)-thiazolines such as 3-methyl-2-benzoylmethylene-β-naphthothiazoline, 3-methyl-2-benzoylmethylene-benzothiazoline, and 3-ethyl-2-propionylmethylene-β-naphtholthiazoline, the rhodanine-based UV initiator comprises one or more of 4-dimethylaminobenzalrhodanine, 4-diethylaminobenzalrhodanine, and 3-ethyl-5-(3-octyl-2-benzothiazolinylidene)-rhodanine, and the other UV initiators comprise one or more selected from phenylacetophenone, hydroxy dimethyl acetophenone, 4,4'-bis(dimethylamino)benzyl, methylbenzoylformate, diphenyl (2,4,6-trimethylbenzoyl)-phosphine oxide, phenyl bis(2,4,6-trimethyl benzoyl), oxy-phenyl-acetic acid-2-[2-oxo-2-phenyl-acetoxy-ethoxy]-ethyl ester, oxy-phenyl-acetic acid-2-[2-hydroxy-ethoxy]-ethyl ester, 4-cyclopentadiene-1-yl) bis[2,6-difluoro-3-(1-H-pyrrole-1-yl)phenyl] titanium, 2-acetylnaphthalene, 2-naphthalaldehyde, iodonium salt, 9.10-anthraquinone, anthracene, pyrene, aminopyrene, perylene, phenanthrene, phenanthrenequinone, 9-fluorenone, dibenzosuberone, curcumin, xanthone, thiomichler's ketone, 2,5-bis(4-diethylaminobenzylidene)cyclopentanone, 2-(4-dimethylamino-benzylidene))-indan-1-one, α-(4-dimethylaminobenzylidene))ketone such as 3-(4-dimethylamino-phenyl)-1-indan-5-yl-propenone, 3-phenylthiophthalimide, N-methyl-3,5-di(ethylthio)-phthalimide, N-methyl-3,5-di(ethylthio)-phthalimide, phenothiazine, methylphenothiazine, N-phenylglycine, amines such as triethanolamine and N-methyldiethanolamine, ethyl-p-dimethylaminobenzoate, 2-(dimethylamino)ethylbenzoate, 2-ethylhexyl-p-dimethylaminobenzoate, octyl-para-N,N-dimethylaminobenzoate, N-(2-hydroxyethyl)-N-methyl-para-toluidine, butoxyethyl 4-dimethylaminobenzoate, 4-dimethylaminoacetophenone, triethanolamine, methyldiethanolamine, dimethylaminoethanol, 2-(dimethylamino)ethyl benzoate, poly(propylene glycol)-4-(dimethylamino)benzoate, and michler's ketone.

3. The UV-curable hydrogel resin according to claim 1, wherein the UV crosslinking agent comprises one or more selected from benzyl methacrylate, lauryl methacrylate, isodecyl methacrylate, phenoxy methacrylate, 2-hydroxyethyl methacrylate, tetrahydro furfuryl methacrylate, cetyl(C16) methacrylate, stearyl methacrylate, methoxyPEG500 methacrylate, methoxyPEG600 methacrylate, methoxyPEG1000 methacrylate, 1,6-hexandiol dimethacrylate, butadiene dimethacrylate, neopentylglycol dimethacrylate, ethyleneglycol dimethacrylate, diethyleneglycol dimethacrylate, triethyleneglycol dimethacrylate, tetraethyleneglycol dimethacrylate, bisphenol A(EO)4 dimethacrylate, bisphenol A(EO)3 dimethacrylate, bisphenol A(EO)10 dimethacrylate, bisphenol A(EO)30 dimethacrylate, 1,3-butyleneglycol dimethacrylate, polyethylene glycol 400 dimethacrylate, polyethylene glycol 200 dimethacrylate, PPG1000(EO)15 dimethacrylate, PPG1000(EO)3 dimethacrylate, trimethylolpropane trimethacrylate, benzyl acrylate, lauryl acrylate, isodecyl acrylate, phenol(EO) acrylate, phenol(EO)2 acrylate, phenol(EO)4 acrylate, phenol(EO)6 acrylate, tetrahydro furfuryl acrylate, nonyl phenol(EO)4 acrylate, nonyl phenol(EO)8 acrylate, nonyl phenol(EO)2 acrylate, ethoxyethoxy ethyl acrylate, stearyl acrylate, 1,6-hexandiol diacrylate, 1,6-hexandiol(EO) diacrylate, butanediol diacrylate, hydroxy pivalic acid neopentyl glycol diacrylate, tripropylene glycol diacrylate, dipropylene glycol diacrylate, bisphenol A(EO)4 diacrylate, bisphenol A(EO)3 diacrylate, tricyclodecane dimethanol diacrylate, tetraethylene glycol diacrylate, polyethylene glycol 400 diacrylate, polyethylene glycol 200 diacrylate, polyethylene glycol 300 diacrylate, polyethylene glycol 600 diacrylate, polypropylene glycol 400 diacrylate, polypropylene glycol 750 diacrylate, bisphenol A(EO)10 diacrylate, bisphenol A(EO)30 diacrylate, tris (2-hydroxy ethyl)isocyanurate diacrylate, trimethylolpropane triacrylate, trimethylolpropane(EO)3 triacrylate, trimethylolpropane(EO)6 triacrylate, trimethylolpropane (EO)9 triacrylate, trimethylolpropane(EO)15 triacrylate, glycerin propoxylated triacrylate, pentaerythritol triacrylate, trimethylolpropane(PO)3 triacrylate, tris(2-hydroxy ethyl) isocyanurate triacrylate, pentaerythritol n-EO tetraacrylate, pentaerythritol tetraacrylate, dipentaerythritol pentaacrylate, dipentaerythritol hexaacrylate, caprolactone acrylate, O-phenylphenol EO acrylate, and methylene bisacrylamide.

4. The UV-curable hydrogel resin according to claim 1, wherein the UV-curable hydrogel resin has a pH of 3 to 9.

5. A UV-curable hydrogel for transdermal administration derived from the UV-curable hydrogel resin according to claim 1, wherein the UV-curable hydrogel exhibits an adhesion of 50 to 120 gf under a peel strength test according to an adhesion test method in the bandage section of the Korean Pharmacopoeia,
wherein a cumulative skin permeation rate of the active ingredient of the UV-hardened hydrogel is 45 to 150 µg/cm$^2$ and a skin permeation speed of the active ingredient of the UV-hardened hydrogel is 2.0 to 7.5 µ µg/cm$^2$/hr for 24 hours, and
wherein a cumulative skin permeation rate of the active ingredient and a skin permeation speed of the active ingredient are measured at 30 to 33° C. under a sink condition using a Franz diffusion cell having an effective area of 0.64 cm$^2$ and an aqueous phase volume of 5.2 ml.

6. A cataplasm, comprising
a drug layer that comprises the UV-curable hydrogel according to claim 5; and
a drug support layer that comprises one or more selected from a polyurethane film, a porous film, a perforated film, a fabric, a nonwoven fabric, and a foam.

7. The cataplasm according to claim 6, wherein the drug layer has an average thickness of 20 to 2,000 µm, and the drug support layer has an average thickness of 7 to 500 µm.

8. The cataplasm according to claim 6, further comprising a peel layer, wherein the peel layer, the drug layer, and the drug support layer are sequentially stacked.

9. The cataplasm according to claim 8, wherein the peel layer has an average thickness of 15 µm to 500 µm and comprises a polymer film coated with a silicone resin or a fluorine resin,
wherein the polymer film comprises one or more polymer compounds selected from polyester; polyvinyl chloride; polyvinylidenechloride; polyethyleneterephtalate; and copolymers thereof.

10. A method for providing anti-inflammation and analgesic effects in a subject in need thereof, comprising administering an effective amount of the cataplasm according to claim 6 to the subject.

11. A UV-curable hydrogel for transdermal administration derived from the UV-curable hydrogel resin according to claim 2, wherein the UV-curable hydrogel exhibits an adhesion of 50 to 120 gf under a peel strength test according to an adhesion test method in the bandage section of the Korean Pharmacopoeia,
wherein a cumulative skin permeation rate of the active ingredient of the UV-hardened hydrogel is 45 to 150 µg/cm$^2$ and a skin permeation speed of the active ingredient of the UV-hardened hydrogel is 2.0 to 7.5 µg/cm$^2$/hr for 24 hours, and
wherein a cumulative skin permeation rate of the active ingredient and a skin permeation speed of the active ingredient are measured at 30 to 33° C. under a sink condition using a Franz diffusion cell having an effective area of 0.64 cm$^2$ and an aqueous phase volume of 5.2 ml.

12. A UV-curable hydrogel for transdermal administration derived from the UV-curable hydrogel resin according to claim 3, wherein the UV-curable hydrogel exhibits an adhesion of 50 to 120 gf under a peel strength test according to an adhesion test method in the bandage section of the Korean Pharmacopoeia,
wherein a cumulative skin permeation rate of the active ingredient of the UV-hardened hydrogel is 45 to 150 µg/cm$^2$ and a skin permeation speed of the active ingredient of the UV-hardened hydrogel is 2.0 to 7.5 µg/cm²/hr for 24 hours, and wherein a cumulative skin permeation rate of the active ingredient and a skin permeation speed of the active ingredient are measured at 30 to 33° C. under a sink condition using a Franz diffusion cell having an effective area of 0.64 cm² and an aqueous phase volume of 5.2 ml.

13. A UV-curable hydrogel for transdermal administration derived from the UV-curable hydrogel resin according to claim 4, wherein the UV-curable hydrogel exhibits an adhesion of 50 to 120 gf under a peel strength test according to an adhesion test method in the bandage section of the Korean Pharmacopoeia, wherein a cumulative skin permeation rate of the active ingredient of the UV-hardened hydrogel is 45 to 150 µg/cm² and a skin permeation speed of the active ingredient of the UV-hardened hydrogel is 2.0 to 7.5 µg/cm²/hr for 24 hours, and wherein a cumulative skin permeation rate of the active ingredient and a skin permeation speed of the active ingredient are measured at 30 to 33° C. under a sink condition using a Franz diffusion cell having an effective area of 0.64 cm² and an aqueous phase volume of 5.2 ml.

* * * * *